(12) United States Patent
Wehrman et al.

(10) Patent No.: US 7,582,417 B2
(45) Date of Patent: Sep. 1, 2009

(54) SEQUENTIAL REPORTER ENZYME LUMINESCENCE (SRL) METHODS AND COMPOSITIONS FOR PRACTICING THE SAME

(75) Inventors: Tom Wehrman, Fremont, CA (US); Georges J. Von Degenfeld, Leverkusen (DE); Helen M. Blau, Menlo Park, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 60 days.

(21) Appl. No.: 11/706,838

(22) Filed: Feb. 14, 2007

(65) Prior Publication Data

US 2007/0224621 A1   Sep. 27, 2007

Related U.S. Application Data

(60) Provisional application No. 60/810,443, filed on Jun. 2, 2006, provisional application No. 60/774,499, filed on Feb. 17, 2006.

(51) Int. Cl.
 *C12Q 1/00* (2006.01)
 *C12Q 1/68* (2006.01)

(52) U.S. Cl. .................... 435/4; 435/6; 435/8
(58) Field of Classification Search .......... 435/4, 435/6, 8
See application file for complete search history.

(56) References Cited

U.S. PATENT DOCUMENTS 5,098,828 A    3/1992  Geiger
6,602,657 B1 *  8/2003  Bronstein et al. ............. 435/4

FOREIGN PATENT DOCUMENTS

WO    WO8702667 A1    5/1987
WO    01/02020    1/2001
WO    01/20331    3/2001

OTHER PUBLICATIONS

Geiger et al., Biol Chem Hoppe Seyler, "A new ultrasensitive bioluminogenic enzyme substrate for beta-galactosidase", Apr. 1992, 373(12):1187-91.
Masuda-Nishimura et al., Lett Appl Microbiol., "Development of a rapid positive/absent test for coliforms using sensitive bioluminescence assay", Feb. 2000, 30(2):130-5.
Miska & Geiger, Biol. Chem. Hoppe. Seyler, "A new type of ultrasensitive bioluminogenic enzyme substrates. I. Enzyme substrates with D-luciferin as leaving group", 1988, 369(5):407-11.
Miska & Geiger, J Clin. Chem. Clin. Biochem., "Synthesis and characterization of luciferin derivatives for use in bioluminescence enhanced enzyme immunoassays. New ultrasensitive detection systems for enzyme immunoassays", 1987, 25(1):23-30.
Shah et al., Mol. Ther., "In vivo imaging of S-TRAIL-mediated tumor regression and apoptosis", 2005, 11(6):926-31.
Springer et al., Mol. Ther., "Localized arteriole formation directly adjacent to the site of VEGF-induced angiogenesis in muscle", Apr. 2003, 7(4):441-9.
von Degenfeld et al., Br J Pharmacol., "Myoblast-mediated gene transfer for therapeutic angiogenesis and arteriogenesis", 2003, 140(4):620-6.
Yang et al., Anal Biochem. , "Homogeneous enzyme immunoassay modified for application to luminescence-based biosensors", 2005, 336(1):102-7.
Shah, Khalid; et al., "In Vivo Imaging of S-TRAIL-Mediated Tumor Regression and Apoptosis", Molecular Therapy, Jun. 2005, 11(6):926-931.
Wehrman, Thomas S.; et al., "Luminescent imaging of beta-galactosidase activity in living subjects using sequential reporter-enzyme luminescence", Nature Methods, Apr. 2006, 3(4)295-301.

* cited by examiner

*Primary Examiner*—Tekchand Saidha
(74) *Attorney, Agent, or Firm*—Bozicevic, Field & Francis LLP; David C. Scherer

(57) ABSTRACT

Sequential reporter enzyme luminescence (SRL) methods are provided. In the subject methods, the activity of a reporter enzyme is evaluated using a secondary reporter system that employs a product of a reporter enzyme mediated reaction as a luminescent substrate, e.g., luciferase substrate. Also provided are kits and other compositions that find use in practicing the subject methods.

51 Claims, 10 Drawing Sheets

SEQUENTIAL REPORTER ENZYME LUMINESCENCE (SRL) METHODS AND COMPOSITIONS FOR PRACTICING THE SAME

CROSS-REFERENCE TO RELATED APPLICATIONS

Pursuant to 35 U.S.C. § 119 (e), this application claims priority to the filing date of the U.S. Provisional Patent Application Ser. No. 60/810,443 filed Jun. 2, 2006 and to the filing date of U.S. Provisional Application Ser. No. 60/774,499 filed Feb. 17, 2006; the disclosures of which applications are herein incorporated by reference.

GOVERNMENT RIGHTS

This invention was made with government support under contracts AG09521, AG20961, HL65572, HD18179 awarded by the National Institutes of Health. The Government has certain rights in this invention.

INTRODUCTION

Luminescence is a phenomenon in which energy is specifically channeled to a molecule to produce an excited state. Return to a lower energy state is accompanied by release of a photon. Luminescence includes fluorescence, phosphorescence, chemiluminescence and bioluminescence. Bioluminescence is the process by which living organisms emit light that is visible to other organisms. Where the luminescence is bioluminescence, creation of the excited state derives from an enzyme catalyzed reaction.

During the past twenty years, high-sensitivity biochemical assays used in research and in medicine have increasingly employed luminescence and fluorescence rather than radioisotopes. This change has been driven partly by the increasing expense of radioisotope disposal and partly by the need to find more rapid and convenient assay methods. More recently, the need to perform biochemical assays in situ in living cells and whole animals has driven researchers toward protein-based luminescence and fluorescence.

Since the cloning of a luciferase from the firefly in 1985 (Wet et al., Proc. Nat'l Acad. Sci. USA (1985) 82:7870-7873), luciferase genes have become essential components of biological research. They are used ubiquitously as reporter genes in cell culture experiments, and their use as reporters has been extended into the context of small animal imaging (Contag et al., Photochem. Photobiol. (1997) 66:523-531). Recently, it has been proposed that the luciferase protein itself could be conjugated to other proteins such as antibodies or growth factors (Park and Gambhir, Proc. IEEE (2005) 93:771-783), and these bioluminescently labeled ligands could then be used for imaging of receptor targets in small animals. The advantage of using a bioluminescent entity to label a protein over similar fluorescent or radioactive approaches, is that in the context of small animal imaging the bioluminescent approach has the potential to be more sensitive (Wu et al., Mol. Ther. (2001) 4: 297-306).

Using in vivo imaging, the course of development, disease progression, and the efficacy or toxicity of drugs can be monitored non-invasively in live animals over time. Of the imaging modalities available, optical techniques based on bioluminescence or fluorescence have emerged as the most accessible and easily manipulated. Bioluminescent imaging (BLI) is characterized by remarkable sensitivity, as background luminescence from tissues is exceedingly low. To date, BLI has been successfully used to monitor biological processes such as cell movement, tumor progression, gene expression, and viral infection in a variety of animal models.

The most widely used BLI method is based on imaging the enzymatic activity of firefly luciferase (FLuc). Due to the spectral properties and lack of toxicity of its substrate, luciferin, FLuc is particularly well suited for in vivo imaging. However, FLuc requires intracellular cofactors such as ATP for activity, limiting its use to cells genetically engineered to express the enzyme. As a result, many useful imaging applications such as monitoring the distribution of circulating factors, detecting extracellular antigen expression, or labeling endogenous cells are not amenable to FLuc imaging. An additional drawback of FLuc is the lack of alternative substrates for detecting FLuc in fixed cells and tissue samples, making it difficult to correlate in vivo imaging with microscopic analysis.

SUMMARY

Sequential reporter enzyme luminescence (SRL) methods are provided. In the subject methods, the activity of a reporter enzyme is evaluated using a secondary reporter system that employs a product of a reporter enzyme mediated reaction as a luminescent substrate. Also provided are kits and other compositions that find use in practicing the subject methods.

DEFINITIONS

Figure 1:
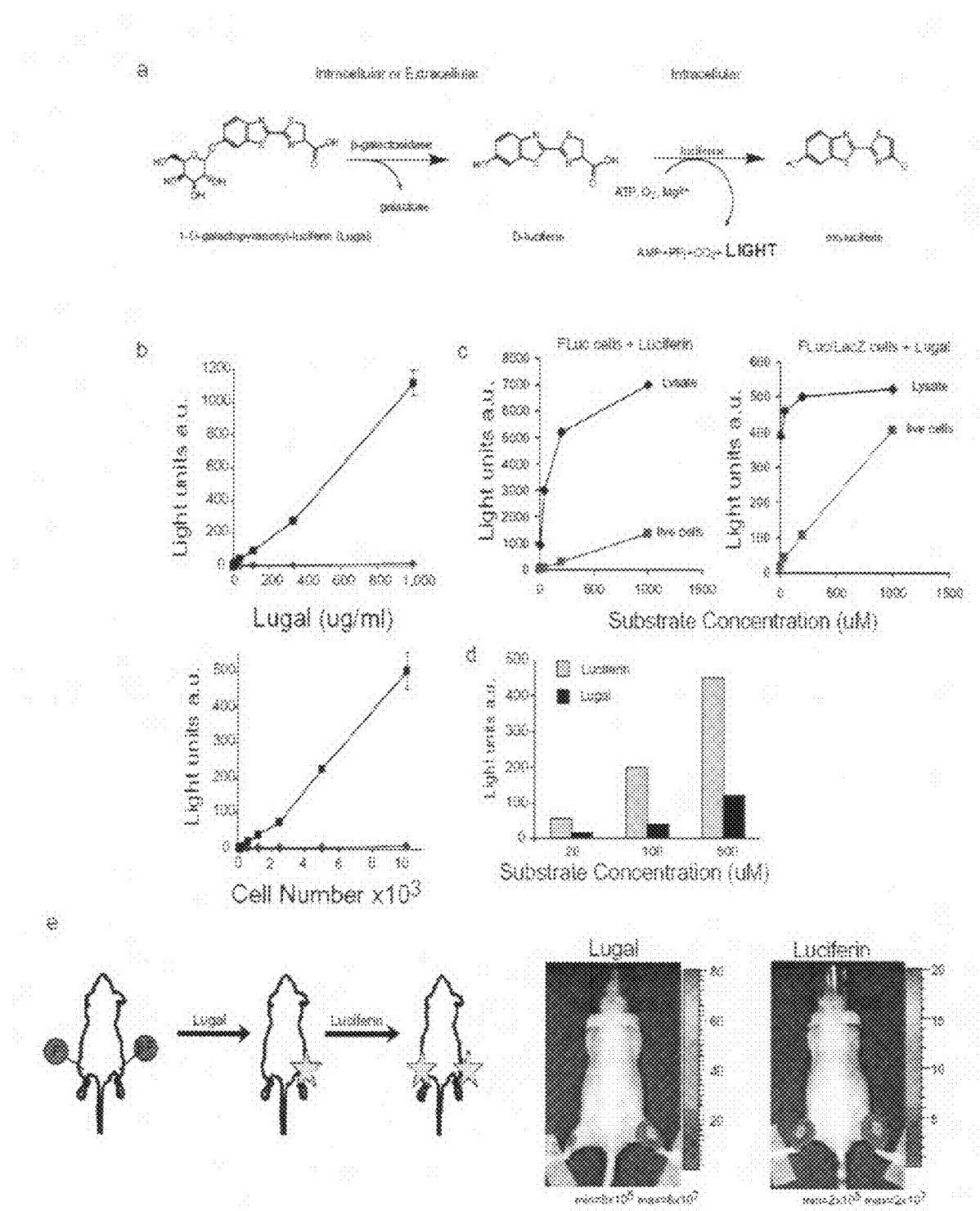
FIG. 1: Luminescent measurement of β-gal activity in living cells using Lugal. (a) Schematic of the SRL β-gal reaction. The galactoside-luciferin conjugate, Lugal, is not a substrate for FLuc but can be cleaved by β-gal to generate free luciferin that is subsequently cleaved by FLuc in a light producing reaction. (b) Lugal can be used to detect β-gal activity in live mammalian cells. $1\times10^4$ FLuc/LacZ C2C12 cells (black line) or cells expressing FLuc alone (red line) were exposed to serial dilutions of Lugal for 10 min. and luminescence was measured by luminometer (upper panel). To determine the linearity of the substrate with respect to cell number, serial dilutions of cells expressing FLuc/LacZ (black curve) or FLuc alone (red line) were made in a 384-well dish and Lugal was added at a concentration of 0.5 mg/ml (lower panel). a.u.=arbitrary units. (c) To determine the cell permeability of Lugal in comparison to luciferin, the amount of light emitted from intact cells and cell lysates was ascertained for both substrates. FLuc cells were plated in a 96-well dish and lysed or washed in PBS. Increasing concentrations of luciferin were added and the luminescence was measured (left panel). The right panel shows FLuc/LacZ cells that were either lysed or rinsed in PBS prior to the addition of increasing amount of Lugal. (d) To determine relative luminescence intensities, different concentrations of either substrate was added to intact FLuc/LacZ cells. Signal intensity of Lugal was approximately one fourth of that obtained with luciferin. (e) β-gal expressing cells can be imaged in a living subject using Lugal. 1 million FLuc cells were injected into the left tibialis anterior (TA) leg muscle of a BALB/c nude mouse and the same number of FLuc/LacZ were injected into the right TA. Lugal was injected after 6 hours, showing a clear luminescent signal over the right leg injected with cells expressing β-gal and FLuc, whereas the left leg showed minimal luminescence (left panel). Luciferin was injected after 24 hours, showing that equivalent cell numbers were present in both legs (right panel). The results are representative of 5 independent experiments. Bioluminescent images are quantified in photons/sec/cm².

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells and Enzymes" (IRL Press, (1986)); B. Perbal, "A Practical Guide To Molecular Cloning" (1984).

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic.

The term "peptide" as used herein refers to any polymer compound produced by amide formation between an α-carboxyl group of one amino acid and an α-amino group of another group.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

As used herein, the term "amino acid" is intended to include not only the L, D- and nonchiral forms of naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine), but also modified amino acids, amino acid analogs, and other chemical compounds which can be incorporated in conventional oligopeptide synthesis, e.g., 4-nitrophenylalanine, isoglutamic acid, isoglutamine, ε-nicotinoyl-lysine, isonipecotic acid, tetrahydroisoquinoleic acid, α-aminoisobutyric acid, sarcosine, citrulline, cysteic acid, t-butylglycine, t-butylalanine, phenylglycine, cyclohexylalanine, β-alanine, 4-aminobutyric acid, and the like. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue). $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243 (1969), 3552-59 is used.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides. As such, a "DNA molecule" refers to the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

A DNA "coding sequence" is a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

The term "oligonucleotide" as used herein denotes single-stranded nucleotide multimers of from about 10 to about 100 nucleotides and up to 200 nucleotides in length.

The term "polynucleotide" as used herein refers to single- or double-stranded polymers composed of nucleotide monomers of generally greater than about 100 nucleotides in length.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

A "vector" is a replicon, such as plasmid, phage or cosmid, to which another DNA segment may be attached so as to bring about the replication of the attached segment.

"DNA regulatory sequences", as used herein, are transcriptional and translational control sequences, such as promoters, enhancers, polyadenylation signals, terminators, and the like, that provide for and/or regulate expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

As used herein, the terms "restriction endonucleases" and "restriction enzymes" refer to bacterial enzymes, each of which cut double-stranded DNA at or near a specific nucleotide sequence.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, heterologous DNA includes coding sequence in a construct where portions of genes from two different sources have been brought together so as to produce a fusion protein product. Allelic variations or naturally-occurring mutational events do not give rise to a heterologous region of DNA as defined herein.

As used herein, the term "reporter gene" refers to a coding sequence attached to heterologous promoter or enhancer elements and whose product may be assayed easily and quantifiably when the construct is introduced into tissues or cells. An example of a "reporter gene" is a nucleic acid encoding a reporter enzyme, i.e., a catalytic product that mediates a reaction of a substrate that produces a detectable signal.

Bioluminescence (BL) is defined as emission of light by living organisms that is well visible in the dark and affects visual behavior of animals (See e.g., Harvey, E. N. (1952). *Bioluminescence*. New York: Academic Press; Hastings, J. W. (1995). Bioluminescence. In: *Cell Physiology* (ed. by N. Speralakis). pp. 651-681. New York: Academic Press.; Wilson, T. and Hastings, J. W. (1998). Bioluminescence. *Annu Rev Cell Dev Biol* 14, 197-230). Bioluminescence does not include so-called ultra-weak light emission, which can be detected in virtually all living structures using sensitive luminometric equipment (Murphy, M. E. and Sies, H. (1990). Visible-range low-level chemiluminescence in biological systems. *Meth. Enzymol.* 186, 595-610; Radotic, K, Radenovic, C, Jeremic, M. (1998). Spontaneous ultra-weak bioluminescence in plants: origin, mechanisms and properties. *Gen Physiol Biophys* 17, 289-308), and from weak light emission which most probably does not play any ecological role, such as the glowing of bamboo growth cone (Totsune, H., Nakano, M., Inaba, H. (1993). Chemiluminescence from bamboo shoot cut. *Biochem. Biophys Res Comm.* 194, 1025-1029) or emission of light during fertilization of animal eggs (Klebanoff, S. J., Froeder, C. A., Eddy, E. M., Shapiro, B. M. (1979). Metabolic similarities between fertilization and phagocytosis. Conservation of peroxidatic mechanism. *J. Exp. Med.* 149, 938-953; Schomer, B. and Epel, D. (1998). Redox changes during fertilization and maturation of marine invertebrate eggs. *Dev Biol* 203, 1-11).

"Optional" or "optionally" means that the subsequently described circumstance may or may not occur, such that the description includes instances where the circumstance occurs and instances where it does not.

"Contacting" means to bring or put together. As such, a first item is contacted with a second item when the two items are brought or put together, e.g., by touching them to each other.

The terms "determining", "measuring", "evaluating", "assessing" and "assaying" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

DETAILED DESCRIPTION

Sequential reporter enzyme luminescence (SRL) methods are provided. In the subject methods, the activity of a reporter enzyme is evaluated using a secondary reporter system that employs a product of a reporter enzyme mediated reaction as a luminescent substrate. Also provided are kits and other compositions that find use in practicing the subject methods.

Aspects of the invention include contacting a multicellular organism or cell that has associated therewith the reporter enzyme and luminescent enzyme, e.g., a luciferase, with a conjugate of a substrate of the reporter enzyme and luminescent enzyme, e.g., a conjugate of a substrate for a galactosidase and a substrate for the luciferase. Signal generated from a luminescent enzyme mediated reaction product of the conjugate is then detected, e.g., to evaluate the activity of the reporter enzyme. Also provided are kits that find use in practicing the subject methods.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the subject invention, the subject SRL methods are reviewed first in greater detail, followed by a review of representative methods in which the subject methods find use, as well as a review of various kits and systems that find use in practicing certain embodiments of the invention.

Sequential Reporter Enzyme Luminescence (SRL) Methods

As summarized above, aspects of the subject methods include evaluating the activity of a reporter enzyme that is associated with a cell and includes a luminescent enzyme, e.g., luciferase, activity. The term "associated" as used herein includes situations where the reporter enzyme is present inside of the cell, i.e., is present at an intracellular location, as well as situations where the reporter enzyme is present on a surface of a cell, i.e., such that it is located at an intracellular location. A feature of embodiments of the subject methods is that the cell is an intact, living cell, by which is meant that the cell is not dead and the cell's membrane has not been structurally compromised, e.g., via permeabilization, lysis, etc.

Aspects of the invention include the use of cells that include a luminescent enzyme activity, i.e., the cells include a bioluminescent protein. By luminescent enzyme activity is meant that the cells include an enzyme that converts a substrate to a luminescent product. Any convenient luminescent enzyme may be present in the cell and employed in the subject methods. Representative luminescent enzymes include, but are not limited to: aequorins, luciferases, and the like.

In certain embodiments, the luminescent enzyme activity is a luciferase activity. While the invention is further described below primarily in terms of these embodiments, it is noted that the invention is not so limited, as the guidance provided with respect to luciferase embodiments is readily modified for embodiments that employ other luminescent enzymes. By "luciferase activity" is meant an activity, e.g., enzymatic activity, that mediates the transition of a luciferin to a luminescent product. Luciferase activities are enzymes which cause bioluminescence, e.g., by combining their substrate (e.g., luciferyl adenylate) with oxygen. Specific luciferases of interest finding use in certain embodiments include, but are not limited to, those reported in U.S. Pat. Nos. 6,737,245; 6,495,355; 6,265,177; 5,814,465; 5,700,673; 5,674,713; 5,670,356; 5,650,289; 5,641,641; 5,618,722; 5,583,024; 5,352,598; 5,330,906; 5,283,179; 5,229,285; and 5 5,221,623; and 5,219,737. In certain embodiments, the luciferase activity is a wild-type luciferase or mutant thereof, where specific luciferases of include the following types of wild-type luciferases or mutants thereof: Coleoptera luciferases, e.g., Lampyridae and Elateridae luciferases, including a *photinus* luciferases, such as luciferases from *Photinus aquilonius, Photinus ardens, Photinus collustrans, Photinus consanguineus, Photinus floridanus, Photinus greeni, Photinus ignitus, Photinus indictus, Photinus macdermotti, Photinus marginellus, Photinus obscurellus, Photinus pyralis* (common eastern firefly), *Photinus sabulosus*, and *Photinus tanytoxus*, where in certain embodiments the luciferase is wild-type *photinus* pyralis luciferase or a mutant thereof.

In certain embodiments, a luciferase expression cassette present in the cell provides for the luciferase activity. In certain embodiments, the luciferase expression cassette is present on a vector that is episomally (i.e., extrachomosomally) maintained in the cell. Expression vectors of interest generally contain a promoter that is recognized by the host organism and is operably linked to the coding sequence for the luciferase coding sequence. Promoters are untranslated sequences located upstream (5') to the start codon of a structural gene (generally within about 100 to 1000 bp) that control the transcription of particular nucleic acid sequence to which they are operably linked. Such promoters typically fall into two classes, inducible and constitutive. Inducible promoters are promoters that initiate increased levels of transcription from DNA under their control in response to some cellular cue, e.g., the presence or absence of a nutrient, a change in temperature or a developmental or activation signal. Any convenient promoter may be employed.

Transcription from vectors in mammalian cells may be controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and most preferably Simian Virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. Also of interest are promoters for snRNAs, e.g. U1 and U6.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs.

In certain embodiments, the expression cassette may be genomically integrated in the target cell, i.e., integrated onto a chromosome of the target cell. A variety of integrating vectors and methodologies for using the same are known in the art and include both site specific and non site-specific integrating systems. For such embodiments, the expression cassette may be placed into a vector that is suitable for use in integrating the expression cassette into the target cell genome, where representative vectors include, but are not limited to: plasmid DNA vectors, retroviral vectors; adeno-associated vectors, adenoviral vectors, double stranded DNA vectors, etc. For example, viral vector delivery vehicles may be employed to integrate an expression cassette into a target cell genome. A variety of viral vector delivery vehicles are known to those of skill in the art and include, but are not limited to: adenovirus, herpesvirus, lentivirus, vaccinia virus and adeno-associated virus (AAV). Transcriptional regulatory elements (promoters, enhancers, terminators, etc.) that find use in genomically-integrated expression cassettes include those noted above for episomal vectors as well as endogenous transcriptional regulatory elements (e.g., as in knock-in gene targeting systems known in the art).

Luciferase expression vectors and methods of using the same, e.g., to transform cells, including cells present in multicellular organisms, are reviewed in U.S. Pat. Nos. 6,737,245; 6,495,355; 6,265,177; 5,814,465; 5,700,673; 5,674,713; 5,670,356; 5,650,289; 5,641,641; 5,618,722; 5,583,024; 5,352,598; 5,330,906; 5,283,179; 5,229,285; and 5,221,623; and 5,219,737, the disclosures of which are herein incorporated by reference.

As reviewed above, in addition to the presence of intracellular luminescent enzyme, e.g., luciferase, activity, the cells employed in the subject methods have a reporter enzyme associated with them, where the term "associated" as used herein includes situations where the reporter enzyme is present inside of the cell, i.e., is present at an intracellular location, situations where the reporter enzyme is present on a surface of a cell, i.e., such that it is located at an extracellular location, as well as situations where the reporter enzyme is present in or on a different cell in close proximity to the cell having the luminescent enzyme. By "close proximity" is meant that a substrate for a luminescent enzyme can readily diffuse from one cell (e.g., the reporter enzyme-containing cell) to the other (e.g., the luminescent enzyme-containing cell). In certain embodiments where the reporter enzyme is present inside of the cell, the reporter enzyme may be provided by the presence of an expression cassette for the reporter enzyme in the cell, e.g., in a manner analogous to the way the luciferase activity is provided, as described above. In these embodiments, the reporter enzyme may be constitutively or inducibly expressed, as desired for a particular application. In yet other embodiments, the reporter enzyme is present on the surface of the cell. The reporter enzyme may be provided on a cell surface using a number of different approaches, e.g., by expressing the reporter enzyme as a fusion partner with a cell surface membrane protein, by having the reporter enzyme specifically bound to a cell surface moiety (such that the reporter enzyme is conjugated to the cell), e.g., by having the reporter enzyme conjugated to a specific binding member pair, such as an antibody or binding fragment/mimetic thereof, a member of a high affinity binding member pair, e.g., biotin/avidin or biotin/streptavidin, etc. As such, a feature of the cell is that it has the reporter enzyme specifically associated with it, either intracellularly, extracellularly or in a cell in close proximity.

Any convenient reporter enzyme may be employed in the subject methods. Specific reporter enzymes that may be employed include, but are not limited to: amidases, aminocyclase I, Arylsulfatase (EC 3.1.6.1), esterases (EC 3.1.1.6), including carboxylesterases ((EC 3.1.1.1) [EC=Enzyme Comission (System) of the International Union for Biochemistry]), carboxypeptidase A and B (EC 3.4.17.1 and EC 3.4.17.2), kininase II (EC 3.4.151), arylsulfatase, alkaline and acid phosphatases (EC 3.1.3.1), lipases (EC 3.1.1.-), acetylesterase, nucleotidases, phospholipase A-D, α- and β-glucosidases (EC 3.2.1.20 and EC 3.2.1.21), α- and β-galactosidases, α- and β-amylases (EC 3.2.1.1 and EC 3.2.1.2); microbial proteinases (EC 3.421.14 or EC 3.4.22.-) and nucleases (EC 3.1.3.-). In certain embodiments, the reporter enzyme is a horseradish peroxidase, alkaline phosphatase, urease, or β-galactosidase.

In certain embodiments, the reporter enzyme includes an enzyme complementation reporter system. By "enzyme complementation reporter system" is meant a system that is made up of two or more fragments of an enzyme (i.e., reporter subunits) that by themselves lack any of the detectable activity (which may be directly or indirectly detectable) that is observed in their parent enzyme but when present together, e.g., within the cytoplasm of a cell, give rise to a detectable amount of the activity of the parent enzyme. One non-limiting example of such an enzyme complementation reporter system is one that includes complementing subunits of β-galactosidase (e.g., the α and ω fragments).

In certain embodiments, the complementation reporter enzyme system is a reduced affinity enzyme complementation system configured for detection of distinct molecular interactions (e.g., protein-protein interactions), where each reporter enzyme subunit is bonded (e.g., as a fusion protein, through a linker, through a non-covalent interaction, etc.) to distinct molecules, e.g., proteins, whose interaction is to be assayed. An aspect of reduced affinity enzyme complementation reporter systems is that at least one of the reporter subunits employed in the system is a variant of a corresponding domain in its wild-type parent enzyme such that its interaction with the other subunits of the system is reversible under assay conditions, absent an interaction mediated by the molecules of interest. As such, reduced-affinity enzyme complementation reporter systems provide for a first detectable signal in the absence of an interaction of interest that is less than a second detectable signal that is observed in the presence of an interaction of interest. Reduced affinity enzyme complementation systems are described in Provisional U.S. Patent Application Ser. No. 60/782,054 filed on Mar. 13, 2006 and entitled "Detection of molecular interactions using a reduced affinity enzyme complementation reporter system", which is incorporated herein by reference in its entirety.

As mentioned above, the cell is contacted with a luminescent enzyme prosubstrate, e.g., luciferase prosubstrate, where the prosubstrate includes both a luminescent enzyme substrate domain (e.g., luciferase substrate domain, aequorin substrate domain, etc.) and a reporter enzyme cleavable domain that, upon contact with the reporter enzyme, is separated (i.e., cleaved) from the luminescent enzyme substrate domain to produce free luminescent enzyme substrate (e.g., luciferase substrate), where the free substrate can then be converted by the luminescent enzyme, e.g., luciferase, of the cell to a luminescent product.

In certain embodiments, the prosubstrate is a conjugate of the luciferase substrate domain and the reporter enzyme cleavable domain. In certain embodiments, the prosubstrate is capable of passing through a cell membrane. In certain embodiments, the size of the prosubstrate is small. As such, the molecular weight of the prosubstrate in certain embodiments is at least about 100 D, such as at least about 400 D and including at least about 500 D, and may be as great as 2000 D or greater, but in certain embodiments does not exceed about 5000 D. In certain embodiments, the prosubstrate exhibits low toxicity, where by low toxicity is meant that the substrate is substantially no more toxic than D-luciferin, where a given substrate is considered to be substantially no more toxic than D-luciferin. In representative embodiments, the $LD_{50}$ of the prosubstrate does not exceed about 5000 mg/kg, and in certain embodiments does not exceed about 1000 mg/kg, and in certain embodiments does not exceed about 20000 mg/kg (for description of $LD_{50}$, see, e.g., the Canadian Center for Occupational Health and Safety website by typing [www.] followed by [ccohs.ca] followed by [/oshanswers/chemicals/Id50] into the address window of a web browser).

The luciferase substrate domain of the prosubstrate may be any convenient luciferase substrate. In certain embodiments, the luciferase substrate domain is a luciferin compound, i.e., a luciferin or a derivative thereof. Luciferins and luciferin derivatives of interest include, but are not limited to: those described in U.S. Pat. Nos. 5,374,535; 5,374,534; 5,128,069; 5,098,828; and 4,826,989; the disclosures of which compounds are herein incorporated by reference.

The reporter enzyme cleavable domain of the prosubstrate may be any convenient moiety, so long as its presence in the prosubstrate at least impairs, if not completely impedes or inhibits, the ability of the luciferase substrate domain from acting as a substrate for luciferase. In certain embodiments, the cleavable domain is one that sterically hinders the ability of luciferase to use the luciferase substrate domain as a substrate, such that the size of the cleavable domain may range from about 10 daltons to about $10^5$ daltons (i.e., 100 kilodaltons), such as from about 100 daltons to about 50 kilodaltons, including from about 1000 daltons to about 10,000 daltons. The particular nature of the cleavable domain depends on the nature of the reporter enzyme whose activity is to be evaluated.

In certain embodiments, the prosubstrate is a D-luciferin derivative of the following general formula (I):

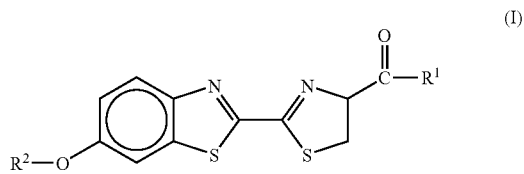

wherein at least one, if not both, of $R_1$ and $R_2$ is the reporter enzyme cleavable domain, where in certain embodiments $R_1$ is a hydroxy or amino group, a linear or branched $C_1$-$C_{20}$ alkoxy or $C_2$-$C_{20}$ alkenyloxy group, an L-amino acid radical, bonded by means of the α-amino group, or an oligopeptide radical with up to 10 L-amino acid units attached by means of the α-amino group of the terminal amino acid units, and $R_2$ is a hydrogen atom, a $H_2PO_3$ or $HSO_3$ group, a linear or branched $C_1$-$C_{20}$ alkyl or $C_2$-$C_{20}$ alkenyl group, optionally substituted by one of more phenyl radicals, an aryl group with 6 to 18 C atoms, a group of the general formula (II)

wherein $R_3$ is a linear or branched $C_1$-$C_{20}$ alkyl or $C_2$-$C_{20}$ alkenyl group, optionally substituted with a phenyl radical, or a $C_6$-$C_{18}$ aryl group, a naturally occurring nucleotide radical with 1 to 3 phosphate groups attached by means of the phosphate group or groups, or a glycosidically attached mono- or disaccharide.

The alkyl or alkoxy groups of the radicals $R_1$, $R_2$ and $R_3$ may be those with 1 to 8, such as 1 to 6 and including 1 to 4 carbon atoms. The alkenyloxy or alkenyl groups of the substituents $R_1$, $R_2$ and $R_3$ may be 2 to 8, such as 2 to 6 and including 2 to 4 carbon atoms. As the L-amino acid radicals, those of naturally occurring amino acids may be used. The oligopeptide is includes these naturally occurring amino acids in certain embodiments. The aryl groups are for example phenyl or naphthyl groups. The monosaccharide consists, for example, of a galactose, glucose, manose or fucose radical. The following compounds may be used as the nucleotides: adenosine, guanosine, thymidine, cytidine or uridine mono-, di- or tri-phosphate.

In certain embodiments of interest, the prosubstrate includes a D-luciferin domain conjugated to a galactosidase substrate domain, where in certain embodiments the substrate is D-luciferin-O-β-galactopyranoside (LuGal).

Contact of the prosubstrate and cell may occur in an in vitro or in vivo format. In vitro formats of interest include cell-based formats, in which contact occurs e.g., by introducing the substrate in a medium, such as an aqueous medium, in which the cell is present. In yet other embodiments, the assay may be in vivo, in which a multicellular organism that includes the cell is employed, and the prosubstrate is contacted with the cell containing multicellular organism. Contact of the targeting vector with the target cell(s) may be accomplished using any convenient protocol. In those embodiments where the target cells are present as part of a multicellular organism, e.g., an animal, the prosubstrate is conveniently administered to (e.g., injected into, fed to, etc.) the multicellular organism, e.g., a whole animal, where administration may be systemic or localized, e.g., directly to specific tissue(s) and/or organ(s) of the multicellular organism. In certain embodiments, the prosubstrate is intraperitoneally administered to the animal.

Multicellular organisms of interest include, but are not limited to: insects cell, vertebrates, such as avian species, e.g., chickens; mammals, including rodents, e.g., mice, rates; ungulates, e.g., pigs, cows, horses; dogs, cats, primates, e.g., monkeys, apes, humans; and the like. As such, the target cells of interest include, but are not limited to: insects cells, vertebrate cells, particularly avian cells, e.g., chicken cells; mammalian cells, including murine, porcine, ungulate, ovine, equine, rat, dog, cat, monkey, and human cells; and the like.

Following contact of the prosubstrate and the target cell(s) as reviewed above, the activity of the reporter enzyme is evaluated or assessed by detecting the presence or absence of signal from luciferase substrate, i.e., by screening the cell (either in vitro or in vivo) for the presence of a luciferase mediated luminescent signal. The detected signal is then employed to evaluate the activity of the reporter enzyme, since the presence of a detected signal is dependent upon an underlying activity of the reporter enzyme.

The luminescent signal produced by the luciferase mediated conversion or the reporter enzyme released luciferase substrate of the prosubstrate may be detected using any convenient luminescent detection device. In certain embodiments, detectors of interest include, but are not limited to: photo-multiplier tubes (PMTs), avalanche photodiodes (APDs), charge-coupled devices (CCDs); complementary metal oxide semiconductors (CMOS detectors) and the like. The detector may be present in a signal detection device, e.g., luminometer, which is capable of detecting the signal once or a number of times over a predetermined period, as desired. Data may be collected in this way at frequent intervals, for example once every 10 ms, over the course of a given assay time period.

In certain embodiments, the subject methods are performed in a high throughput (HT) format. In the subject HT embodiments of the subject invention, a plurality of different cells are simultaneously assayed or tested. By simultaneously tested is meant that each of the cells in the plurality are tested at substantially the same time. In general, the number of cells that are tested simultaneously in the subject HT methods ranges from about 10 to 10,000, usually from about 100 to 10,000 and in certain embodiments from about 1000 to 5000. A variety of high throughput screening assays for determining the activity of candidate agent are known in the art and are readily adapted to the present invention, including those described in e.g., Schultz (1998) Bioorg Med Chem Lett 8:2409-2414; Weller (1997) Mol. Divers. 3:61-70; Fernandes (1998) Curr Opin Chem Biol 2:597-603; Sittampalam (1997) Curr Opin Chem Biol 1:384-91; as well as those described in published United States application 20040072787 and issued U.S. Pat. No. 6,127,133; the disclosures of which are herein incorporated by reference.

In certain embodiments, the methods are employed in an in vivo bioluminescent imaging protocol, where such protocols include, but are not limited to, those described in U.S. Pat. Nos. 6,939,533; 6,923,951; 6,916,462; 6,908,605; 6,890,515; 6,649,143; 6,495,355; 6,217,847; and 5,650,135. In such embodiments, the methods may include immobilizing a multicellular animal that includes the subject cell(s) and prosubstrate, and then detecting signal from the animal using whole animal imaging techniques.

In certain embodiments, the methods included introducing the reporter enzyme to a multicellular organism at some point prior to signal detection. For example, where the reporter enzyme is to be employed for extracellular localization applications, the reporter enzyme may be conjugated to a target moiety for the target cell of interest that is to be localized, and the conjugate administered to the organism, e.g., as reviewed in U.S. Pat. Nos. 6,939,533; 6,923,951; 6,916,462; 6,908, 605; 6,890,515; 6,649,143; 6,495,355; 6,217,847; and 5,650, 135.

The targeting moiety may be any convenient moiety, where the target moiety is, in many embodiments, properly viewed as an "affinity agent." In certain embodiments, the affinity agent (i.e., targeting moiety) is a molecule that has a high binding affinity for a target cell, and specifically structure on the target cell. By high binding affinity is meant a binding affinity of at least about $10^{-4}$ M, such as at least about $10^{-6}$ M or higher, e.g., $10^{-9}$M or higher. The affinity agent may be any of a variety of different types of molecules, so long as it exhibits the requisite binding affinity for the target cell when immobilized on the surface of a substrate.

In certain embodiments, the affinity agent is a small molecule or large molecule ligand. By small molecule ligand is meant a ligand ranging in size from about 50 to about 10,000 daltons, usually from about 50 to about 5,000 daltons and more usually from about 100 to about 1000 daltons. By large molecule is meant a ligand ranging in size from about 10,000 daltons or greater in molecular weight.

The small molecule may be any molecule, as well as binding portion or fragment thereof, that is capable of binding with the requisite affinity to the target cell. Generally, the small molecule is a small organic molecule that is capable of binding to the target cell of interest. The small molecule will include one or more functional groups necessary for structural-interaction with the target cell, e.g., groups necessary for hydrophobic, hydrophilic, electrostatic or even covalent interactions. Where the affinity agent is one that binds to a target cell via a cell surface protein, the agent will include functional groups necessary for structural interaction with proteins, such as hydrogen bonding, hydrophobic-hydrophobic interactions, electrostatic interactions, etc., and will typically include at least an amine, amide, sulfhydryl, carbonyl, hydroxyl or carboxyl group, preferably at least two of the functional chemical groups.

Small molecule affinity agents may include cyclical carbon or heterocyclic structures and/or aromatic or polyaromatic structures substituted with one or more of the above functional groups. Also of interest as small molecules are structures found among biomolecules, including peptides, saccharides, fatty acids, steroids, purines, pyrimidines, derivatives, structural analogs or combinations thereof. Such compounds may be screened to identify those of interest, where a variety of different screening protocols are known in the art.

The small molecule may be derived from a naturally occurring or synthetic compound that may be obtained from a wide variety of sources, including libraries of synthetic or natural compounds. For example, numerous means are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc. to produce structural analogs.

As such, the small molecule may be obtained from a library of naturally occurring or synthetic molecules, including a library of compounds produced through combinatorial means, i.e., a compound diversity combinatorial library. When obtained from such libraries, the small molecule employed will have demonstrated some desirable affinity for the protein target in a convenient binding affinity assay. Combinatorial libraries, as well as methods for the production and screening, are known in the art and described in: U.S Pat. Nos. 5,741,713; 5,734,018; 5,731,423; 5,721,099; 5,708,153; 5,698,673; 5,688,997; 5,688,696; 5,684,711; 5,641,862; 5,639,603; 5,593,853; 5,574,656; 5,571,698; 5,565,324; 5,549,974; 5,545,568; 5,541,061; 5,525,735; 5,463,564; 5,440,016; 5,438,119; 5,223,409, the disclosures of which are herein incorporated by reference.

Also suitable for use as binding domains are polynucleic acid aptimers. Polynucleic acid aptamers may be RNA oligonucleotides which may act to selectively bind proteins, much in the same manner as a receptor or antibody (Conrad et al., Methods Enzymol. (1996), 267 (Combinatorial Chemistry), 336-367). In certain embodiments where the affinity ligand is a nucleic acid, e.g., an amptamer, the target analyte is not a nucleic acid. In certain embodiment, the affinity ligand is not a nucleic acid.

As pointed out, the affinity agent can also be a large molecule. Of particular interest in certain embodiments as large molecule affinity agents are antibodies, as well as binding fragments and mimetics thereof. Where antibodies are the affinity agent, they may be derived from polyclonal compositions, such that a heterogeneous population of antibodies differing by specificity are each tagged with the same tag nucleic acid, or monoclonal compositions, in which a homogeneous population of identical antibodies that have the same specificity for the target protein are each tagged with the same tag nucleic acid. As such, the affinity agent may be either a monoclonal and polyclonal antibody. In yet other embodiments, the affinity agent is an antibody binding fragment or mimetic, where these fragments and mimetics have the requisite binding affinity for the target protein. For example, antibody fragments, such as Fv, F(ab)$_2$ and Fab may be prepared by cleavage of the intact protein, e.g., by protease or chemical cleavage. Also of interest are recombinantly produced antibody fragments, such as single chain antibodies or scFvs, where such recombinantly produced antibody fragments retain the binding characteristics of the above antibodies. Such recombinantly produced antibody fragments generally include at least the VH and VL domains of the subject antibodies, so as to retain the binding characteristics of the subject antibodies. These recombinantly produced antibody fragments or mimetics of the subject invention may be readily prepared using any convenient methodology, such as the methodology disclosed in U.S. Pat. Nos. 5,851,829 and 5,965,371; the disclosures of which are herein incorporated by reference.

The above described antibodies, fragments and mimetics thereof may be obtained from commercial sources and/or prepared using any convenient technology, where methods of producing polyclonal antibodies, monoclonal antibodies, fragments and mimetics thereof, including recombinant derivatives thereof, are known to those of the skill in the art.

In certain embodiments, the methods may include inducing expression of the reporter enzyme, e.g., by contacting the cell with a suitable expression inducer.

Utility

Embodiments of the invention find use in a variety of different applications. Representative uses are described below, where the following described uses are merely representative and are in no way meant to limit the use of the subject proteins to those described below. Embodiments of the invention find use in applications where intact cells that include the reporter enzyme are employed, e.g., for screening compounds for activity of interest. Embodiments of the invention also find use in in vivo marker or imaging applications, where the localized activity of a reporter enzyme is imaged in vivo, e.g., to assess gene expression patterns, to localize particular cell populations, etc. Representative in vivo imaging applications in which embodiments of the invention find use include, but are not limited to, those described in U.S. Pat. Nos. 6,939,533; 6,923,951; 6,916,462; 6,908,605; 6,890,515; 6,649,143; 6,495,355; 6,217,847; and 5,650,135, as well as those types of applications exemplified below in the Experimental Section.

As indicated above, the present invention finds use in monitoring gene expression in a cell (or cells) grown in vitro. In certain in vitro embodiments, cells are generated that constitutively express luciferase and harbor a reporter gene construct in which reporter gene expression is controlled by a promoter/enhancer of interest (e.g., a promoter that is turned on in response to a specific cellular cue or one that is indicative of a specific cellular process, e.g., apoptosis). In these embodiments, the cells are cultured under specific user-defined conditions (e.g., in the presence or absence of a cytokine, nutrient and/or candidate therapeutic agent), exposed to the cognate prosubstrate and monitored for emitted light. Higher light emission indicates higher reporter gene expression and lower light emission indicates lower reporter gene expression. This type of assay finds use in numerous in vitro applications, including drug screening (e.g., high throughput (HT) drug screening), studies of signal transduction pathway, in vitro developmental studies (e.g., neuronal cell differentiation, stem cell growth and differentiation, etc); see below for additional genes/cellular processes of interest.

In certain other in vitro embodiments, the cells of interest express both the luciferase and reporter gene under different non-constitutive promoters (e.g., promoters that are induced under specific conditions, e.g., during terminal differentiation of a cell). In these embodiments, the cells are again cultured under specific user-defined conditions, exposed to the cognate prosubstrate and monitored for emitted light. Detection of light emission indicates that the promoters for both the luciferase and reporter gene under the specific culture conditions. In this way, the co-regulation of two genes can be determined. In a variation of this embodiment, a second reporter gene (i.e., a reporter gene having a different cognate prosubstrate specificity) can also be introduced into the cell. In these embodiments, exposing the cell to the cognate prosubstrate for the first reporter will indicate whether the first reporter gene is co-expressed with luciferase whereas exposing the cell to the cognate substrate for the second reporter will indicate whether the second reporter gene is co-expressed with luciferase. As with the previously described in vitro assays, these assays find use in numerous in vitro applications, including drug screening (e.g., high throughput (HT) drug screening), signal transduction pathway studies, in vitro developmental studies (e.g., neuronal cell differentiation, stem cell growth and differentiation, etc). Furthermore, in certain embodiments, the luciferase is constitutively expressed while multiple distinct reporter genes are under the control of regulated (or regulatable) promoters.

In another example, the present invention finds use in monitoring spatial and temporal gene expression in vivo. Mice engineered to express a reporter gene under the control of a specific promoter (and luciferase under a constitutive or non-constitutive promoter) can be injected with the prosubstrate and monitored for light emission from the animal. As with the in vitro embodiments above, in vivo methods of using the reporter genes and cognate substrates of the invention find use in numerous applications, including monitoring developmental processes as well as monitoring the effect of agents or other treatments on gene expression in vivo (see exemplary genes/processes of interest discussed below).

In yet another example, the present invention finds use in determining the localization and/or the abundance of a specific cell in vivo. For example, cells expressing the reporter gene and luciferase can be injected into an animal and monitored over time by injecting the prosubstrate into the animal and detecting light emission. In yet other embodiments, cells can be labelled on their surface with reporter enzyme in vitro, e.g., by conjugating the reporter enzyme to the cell surface, and then injecting those labeled cells and tracking them by injecting the prosubstrate in vivo. In certain embodiments, the cell injected into the luciferase expressing animal is a reporter enzyme expressing bacterium. For example, bacteria expressing beta-galactosidase may be injected into luciferase expressing mice. In such embodiments, cleaved prosubstrate would produce light in the surrounding tissue expressing luciferase. In another example, an animal expressing luciferase can be injected with an affinity agent that is specific for a moiety on a cell coupled to a reporter enzyme (e.g., an antibody specific for the T cell marker CD4 coupled to β-galactosidase) followed by injection of the prosubstrate and detection of emitted light. In both of these cases, both the abundance and location of the cells of interest can be determined. There are numerous uses for this type of assay in a wide range of fields, including developmental biology, immunology and oncology, just to mention a few.

In certain embodiments of the invention, one can employ multiple reporter enzymes and multiple cognate prosubstrates in practicing the disclosed methods. For example, a transgenic mouse line can be generated that expresses two (or more) distinct reporter enzymes under the control of different promoters (as well as luciferase). Detection of cells expressing the first reporter enzyme is done by injecting the animal with the first prosubstrate (i.e., one that is cleaved by the first reporter enzyme, thereby releasing a luciferase substrate) into the animal and detecting the emitted light. Detection of cells expressing the second reporter enzyme is done by injecting the animal with the second prosubstrate (i.e., one that is cleaved by the second reporter enzyme, thereby releasing a luciferase substrate) into the animal and detecting the emitted light. This allows cells expressing one or both of the reporter enzymes to be detected. Injection of the prosubstrates can be done simultaneously, consecutively, into different animals, or in any other manner as is best suited for the objectives of the assay. This example is merely illustrative of the types of assays that can be performed using multiple reporter enzymes and multiple cognate prosubstrates in the cell detection methods of the invention and as such, no limitation with regard to this aspect of the invention is intended.

In certain embodiments, the methods may further include a step of the contacting the cell, e.g., in vivo or in vitro, with a free version of the luciferase substrate, e.g., a version of the substrate which is not conjugated to a substrate for the reporter enzyme. For example, one can have a method in which a cell or animal comprising the same is contacted first with Lugal followed by luciferin, e.g. to image βgal targeted tumor cells via the lugal generated signal followed by luciferin injection to image the tumor size.

As indicated above, the system and methods of the present invention finds use in monitoring the expression of a gene (or genes) of interest either in a cell in vitro and/or in vivo. Genes of interest include, but are not limited to, genes associated with tumorigenesis and cell transformation; angiogenic or anit-angiogenic genes; genes associated with tissue repair; genes associated with stem cell growth, maintenance and differentiation; immunomodulator genes, such as those associated with inflammatory and autoimmune responses; ligand receptor genes; genes associated with neurodegenerative disorders; genes under the control of specific transcription factors; genes involved in cardiovascular diseases; genes involved in regulating different metabolic processes in different tissues and organs (e.g., body weight regulation, regulation of bone formation, etc.), etc. Exemplary genes associated with certain of these processes follows.

Examples of genes associated with tumorigenesis and cell transformation include multidrug resistance genes (Nieth, et al., FEBS Lett. 545:144 (2003); Wu, et al, Cancer Res. 63:1515 (2003)), cyclins (Li, et al., Cancer Res. 63:3593 (2003); Zou, et al., Genes Dev. 16:2923 (2002)), β-Catenin (Verma, et al., Clin Cancer Res. 9:1291 (2003)), telomerase genes (Kosciolek, et al., Mol Cancer Ther. 2:209 (2003)), c-MYC, N-MYC, BCL-2, ERBB1 and ERBB2 (Nagy, et al. Exp. Cell Res. 285:39 (2003)). Genes encoding proteins associated with tumor migration are also of interest, e.g., integrins, selectins and metalloproteinases.

Examples of genes associated with angiogenesis include Vascular Endothelial Growth Factor (VEGF) (Reich, et al., Mol. Vis. 9:210 (2003)) and VEGFR; Tie-2 and angiopoietin (Pediatr Endocrinol Rev. 2005 March; 2(3):399-408); EphB4 and EphrinB2 (EMBO J. 2006 Feburary. 8; 25(3):628-41); ELF-1 (Blood. 2006 April. 15; 107(8):3153-60); heparanase, ApoB 100, CETP, sPLA2, and TE2. Examples of anti-angiogenic genes include, but are not limited to, endostatin (see e.g., U.S. Pat. No. 6,174,861); angiostatin (see, e.g., U.S. Pat. No. 5,639,725); and VEGF-R2 (see e.g., Decaussin et al. (1999) J. Pathol. 188(4): 369-737).

Examples of immunomodulatory genes include cytokines such as growth factors (e.g., TGF-α, TGF-β, EGF, FGF, IGF, NGF, PDGF, CGF, GM-CSF, SCF, etc.), interleukins (e.g., IL-2, IL-3, IL-4, IL-6, IL-7, IL-10, IL-12, IL-15, IL-20, etc.), interferons (e.g., IFN-α, IFN-β, IFN-γ, etc.), TNF (e.g., TNF-α), and Flt3-Ligand. Fas and Fas Ligand genes are also immunomodulator target sequences of interest (Song, et al., Nat. Med. 9:347 (2003)). Genes encoding secondary signaling molecules in hematopoietic and lymphoid cells are also of interest, e.g., Tec family kinases, such as Bruton's tyrosine kinase (Btk) (Heinonen, et al., FEBS Lett. 527:274 (2002)).

Examples of cell receptor ligands include ligands that are able to bind to cell surface receptors (e.g., insulin receptor, EPO receptor, G-protein coupled receptors, receptors with tyrosine kinase activity, cytokine receptors, growth factor receptors, etc.), to modulate (e.g, inhibit, activate, etc.) the physiological pathway that the receptor is involved in (e.g., glucose level modulation, blood cell development, mitogenesis, etc.). Examples of cell receptor ligands include cytokines, growth factors, interleukins, interferons, erythropoietin (EPO), insulin, glucagon, G-protein coupled receptor ligands, etc.).

Examples of tumor suppressor genes include, but are not limited to, p 53 (Lamb et al., Mol. Cell. Biol. 6:1379-1385 (1986), Ewen et al., Science 255:85-87 (1992), Ewen et al. (1991) Cell 66:1155-1164, and Hu et al., EMBO J. 9:1147-1155 (1990)), RB1 (Toguchida et al. (1993) Genomics 17:535-543), WT1 (Hastie, N. D., Curr. Opin. Genet. Dev. 3:408-413 (1993)), NF1 (Trofatter et al., Cell 72:791-800 (1993), Cawthon et al., Cell 62:193-201 (1990)), VHL (Latif et al., Science 260:1317-1320 (1993)), APC (Gorden et al., Cell 66:589-600 (1991)), DAP kinase (see e.g., Diess et al. (1995) Genes Dev. 9: 15-30), p 16 (see e.g., Marx (1994) Science 264(5167): 1846), ARF (see e.g., Quelle et al. (1995) Cell 83(6): 993-1000), Neurofibromin (see e.g., Huynh et al. (1992) Neurosci. Lett. 143 (1-2): 233-236), and PTEN (see e.g., Li et al. (1997) Science 275(5308): 1943-1947).

Examples of components of signal transduction pathways include G-protein coupled receptors (GPCRs), G-proteins, GTPase activating protein (GAP), adenylyl cyclase, protein kinases, proteins containing protein-protein interaction domains (e.g., SH2, SH3, PTB, WW, FHA, SAM, LIM, PX, EH, EVH1 AND PDZ domains), CDB coactivator protein, CREB transcription factor, cAMP response elements, STAT transcription factors, β-catenin/LEF1 transcription factor, Smad transcription factors, zinc finger transcription factors, protein kinase C, phospholipase, PI-3 kinases, ion channels, calmodulin, and cytoplasmic guanylyl cyclase, c-fos, and NFAT. For other examples, see Hunter, Cell 100:113-127 (2000).

Examples of genes associated with myofiber repair and/or muscle stem cells include Myf5, muscle specific p38 MAPK, Myod, Myogenin, MRF4 (Biochem Biophys Res Commun. 2002 Nov. 22; 299(1):7-13); α-7 integrin (Exp Cell Res. 2001 May 1; 265(2):212-20); Pax 7 and Pax 3 (J Cell Biol. 2006 January. 2; 172(1):91-102). Examples of genes associated with bone repair include BMPs (Clin Podiatr Med Surg North Am. 2005 October; 22(4):607-18, vii) and Noggin (Mol. Ther. 2005 August; 12(2):239-46).

There are also genes that are known to be induced in response to exposure to certain environmental stimuli and/or toxic. Examples of such genes are genes that are induced by UV damage, induction of DNA repair genes, and genes involved in apoptosis. Genes which respond in a characteristic manner to such environmental/toxic stimuli have been called damage-inducible or stress-related genes (MacGregor, J. T., et al., Fundamental and Applied Toxicology, 26:156-173, 1995).

There are also numerous genes which have been shown to be involved in the following physiological functions: pain and/or inflammation (e.g., endorphins and enkephalins); organ inflammation (TGF-β-1); fever (IL-1α/β; TNF α/β, IFN α, IL-6); cell proliferation (PCNA, TNF); development (bmp4-defective gastrulation, mesoderm formation, bmp5-skeletal defects, bmp7-kidney, eye, skeletal); drug metabolism (e.g., oxidation, NO (nitric oxide) synthesis and degradation; N-acetylation; and S-methylation); apoptosis (e.g., FAS, ICE, Bax, Bcl-2); infectious diseases (e.g., chlamydia, toxoplasma); and cell necrosis (TNF, TGF-β-1).

Therefore, embodiments of the invention find use in a wide variety of different applications, only a few of which are mentioned above.

Kits

Also provided by the subject invention are kits for use in practicing one or more of the above described methods, where the subject kits may include a prosubstrate (e.g., as reviewed above) and at least one of: (i) a cell that that includes a nucleic acid encoding the reporter enzyme corresponding to the prosubstrate and a nucleic acid encoding a luciferase; (ii) a multicellular organism, e.g., transgenic animal, that includes at least one of a cell that includes a nucleic acid encoding said reporter enzyme and a cell that includes a nucleic acid encoding a luciferase; and (iii) a conjugate of the reporter enzyme and a targeting moiety, e.g., an affinity agent. Also present may be other agents that find use in various applications.

The various components of the kits may be present in separate containers, or at least some of the components may be precombined in a single container, as feasible and/or desirable.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are offered by way of illustration and not by way of limitation.

Experimental

EXAMPLE I

I. Materials and Methods

A. Cell Lines and In Vitro Experiments

The LacZ retroviral construct used was previously described (Mohler, W. A. & Blau, H. M. Gene expression and cell fusion analyzed by lacZ complementation in mammalian cells. Proc Natl Acad Sci USA 93, 12423-7 (1996)). The PGL3 luciferase gene (Promega) was PCR amplified and placed into an MFG vector previously engineered to express lyt-2, the murine gene encoding CD8 from an IRES (Wehrman, T. S., Casipit, C. L., Gewertz, N. M. & Blau, H. M. Enzymatic detection of protein translocation. Nat Methods 2, 521-7 (2005)). The parental MFG-IRES-lyt-2 construct was used to generate the lyt-2 expressing myoblasts. Retroviral transduction was performed using the ecotropic ΦNX packaging cell line (generous gift of GP Nolan). This line was transiently transfected with the proviral constructs using Fugene transfection reagent (Boehringer Mannheim). The supernatant from the transfected cells was removed 24-72 hours later and applied to C2C12 myoblasts that were grown in DMEM (Invitrogen) and 20% FBS (Hyclone). Polybrene was added to a final concentration of 8 μg/ml (Sigma) and cells were spun at 2,000 RPM in a Beckman GS-6 centrifuge. Cells transduced with the Luciferase-IRES-lyt-2 construct or the parental MFG-IRES-lyt-2 construct were stained with an anti-lyt-2 antibody conjugated to APC (BD Pharmingen). Cells were sorted by FACS on a Becton Dickinson flow cytometer with MoFlo electronics. Lugal (special order from Promega) was resuspended in distilled water, aliquotted and stored at −20° C. For the in vitro cell studies, C2C12 cells were seeded in growth medium into a 384-well dish. 3 hours later cells were treated with the indicated Lugal concentration and incubated for 15 min. The plate was read on a Tropix TR717 luminometer at room temperature with an integration time of 1 s/well. For the comparison of Lugal and luciferin membrane permeability, cells (either Fluc or LacZ/Fluc) were plated overnight in a 96-well dish. Cell lysates were prepared by aspirating the media and adding 15 ul of lysis buffer (1% Triton-X100, 50 mM Tris-HCl, 10 mM MgCl2, 10 mM DTT, 1 mM ATP, pH 7.5). For wells with intact cells, 15 ul of PBS was substituted for lysis buffer. The substrates were added at equivalent volumes to bring the reaction volume to 30 ul.

B. Antibody Conjugation

β-gal was purchased from Sigma. Bio-Gel P-30 size exclusion resin and Bio-Spin disposable columns were from Bio-Rad. Succinimidyl-4-(N-maleimidomethyl)cyclohexane-1-carboxylate (SMCC) was obtained from Pierce. CD4 antibody (clone RM4-5) was kindly provided by BD Pharmingen. β-gal was resuspended in PBS at 10 mg/ml and purified on a P-30 column equilibrated in PBS to remove residual Tris salts. SMCC (100 equivalents) was added and the reaction was allowed to proceed for 1 hour. The reaction was then exchanged into "coupling buffer" (50 mM MES, 2 mM EDTA, pH 6.0) on a P-30 column. Concurrently, antibody (0.5 mg/ml) was reduced with 20 mM dithiothreitol for 30 min, then exchanged into coupling buffer on a P-30 column. The reduced antibody was added to the β-gal-SMCC in a 2-6 fold molar excess, and the coupling was allowed to proceed for 1 hour. The reaction was quenched by addition of 100 equivalents of β-mercaptoethanol for 30 min. After pelleting to remove precipitated products, the reaction was purified on a P-30 column equilibrated in PBS to obtain CD4-β-Gal.

C. Animals and Bone Marrow Transplant

All protocols were approved by the Administrative Panel on Laboratory Animal Care at Stanford University School of Medicine. The L2G85 mouse strain ubiquitously expressing FLuc under control of the β-actin promoter (FLuc mouse) (Cao, Y. A. et al. Molecular imaging using labeled donor tissues reveals patterns of engraftment, rejection, and survival in transplantation. Transplantation 80, 134-9 (2005)) used as "universal donor" in all transgenic studies and the Myf5nLacZ mouse strain (Tajbakhsh, S. et al. Gene targeting the myf-5 locus with nlacZ reveals expression of this myogenic factor in mature skeletal muscle fibres as well as early embryonic muscle. Dev Dyn 206, 291-300 (1996)) were kind gifts from C. H. Contag (Stanford University Medical School, Stanford) and B. J. Wold (California Institute of Technology, Pasadena) respectively. BALB/c nude and FVB mice were obtained from the Stanford University in-house colony. Bone marrow was harvested from femurs and tibias of transgenic FLuc mice, and $10^7$ bone marrow cells were transplanted by tail-vein injection into lethally irradiated 8-week-old FVB mice.

D. Cell Injections and Imaging

Imaging was performed using a Xenogen-100 device as previously described (Cao et al., supra). Briefly, the system is comprised of a light-tight imaging chamber, a cooled digital CCD camera with a cryogenic refrigeration unit and the appropriate computer system (Living Image™ 2.50 software, Xenogen, Alameda). Following intraperitoneal injection of luciferin or Lugal at equimolar concentrations in 100 μl PBS (0.1 mmol/kg body weight unless otherwise indicated), images were continuously acquired up to 2 hours and stored for subsequent off-line analysis. Images were analyzed between 5 and 15 minutes after Lugal injection unless otherwise indicated. C2C12 myoblasts were harvested and suspended in 0.5% BSA in PBS at a final concentration of $10^8$ cells/ml for injection. For experiment shown in FIG. 1e, $10^6$ cells expressing LacZ and FLuc (FLuc/LacZ cells) were injected into the right tibialis anterior muscle (TA) and $10^6$ cells expressing FLuc only (FLuc cells) into the left TA of BALB/c nude mice. Either Lugal or luciferin was injected intraperitoneally at different time points between 6 hours and 7 days after cell implantation. For experiment shown in FIGS. 2a and 2b, a range of cell numbers between $5\times10^4$ and $2\times10^6$ were injected subcutaneously in 10 different locations of the back of BALB/c nude mice. Lugal or luciferin was injected intraperitoneally at approximately 6 (Lugal) and 12 (luciferin) hours after cell implantation (0.5 mmol/kg body weight) and images analyzed between 20 and 40 mins after substrate injection. The experiment was performed three times with similar results.

E. Myf5nLacZ/FLuc Transgenic Mice

Mice heterozygous for Myf5nLacZ were crossed with homozygous FLuc mice and the F1 offspring was genotyped (Tajbakhsh et al., supra). Myf5nLacZ+/FLuc+ mice were compared with Myf5nLacZ−/FLuc+ littermates as negative controls. Muscle damage was induced as previously described (Palermo, A. T., Labarge, M. A., Doyonnas, R., Pomerantz, J. & Blau, H. M. Bone marrow contribution to skeletal muscle: a physiological response to stress. Dev Biol 279, 336-44 (2005)) by a single 10-μl dose of notexin (10 μg/ml) injected into the left TA of Myf5nLacZ/FLuc and Myf5nLacZ-negative littermates (n=2/per group). Imaging was performed by intraperitoneal Lugal injection on 2 consecutive days prior to notexin injection, and 1, 3, 4, 5, 6, 7, 8, 9, 11 and 15 days thereafter. Regions of interest over each TA was quantified in photons/cm²/sec. For each measurement, a ratio was obtained from the treated and non-treated legs from each mouse then expressed as a % of the initial pre-treatment values.

E. Detection of Extracellular β-Gal Activity

Figure 3:
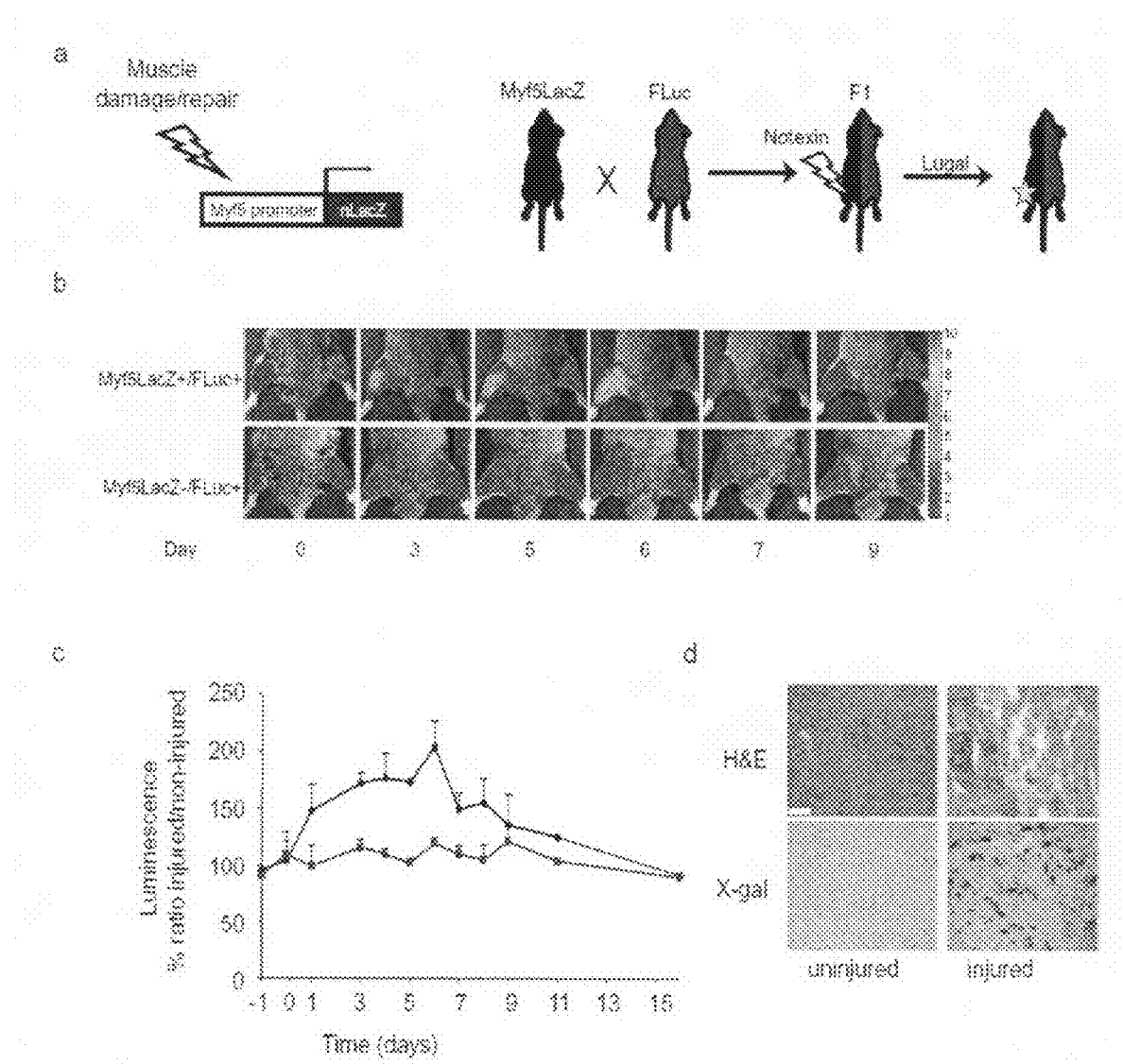
FIG. 3: Luminescent imaging of muscle regeneration over time in transgenic Myf5nLacZ reporter mice. (a) A directly-applicable mouse model for bioluminescent imaging of myoblast activation in regenerating muscle was generated by crossing a transgenic mouse heterozygous for the Myf5nLacZ construct with a FLuc mouse. (b) The Myf5nLacZ+/FLuc+ F1 offspring (top panels) were compared with their Myf5nLacZ−/FLuc+ littermates (lower panels) after damage to the left TA by intramuscular notexin injection. A clear, progressive increase in signal intensity can be seen over the left leg of the Myf5nLacZ+/FLuc+ starting 24 hours after notexin injection, peaking between days 3 and 4 and gradually returning to baseline thereafter. No signal increase is seen over the left, notexin-injected leg of the Myf5nLacZ−/FLuc+ littermate. (c) Luminescence was quantified and the signal over the right, notexin-injected leg was normalized to the left control leg (average±standard deviation, n=2/group). A relative signal increase up to 2-fold can be seen in the TA of the Myf5nLacZ+/FLuc+ mice whereas no difference between the legs was obtained from the control littermate that was also treated with notexin. (d) X-gal staining shows little β-gal activity in Myf5nLacZ+ mice without muscle damage (lower left), but clear β-gal staining in regenerating TA muscle 4 days after notexin injection (lower right). Scale bar=50 μm.
Figure 4:
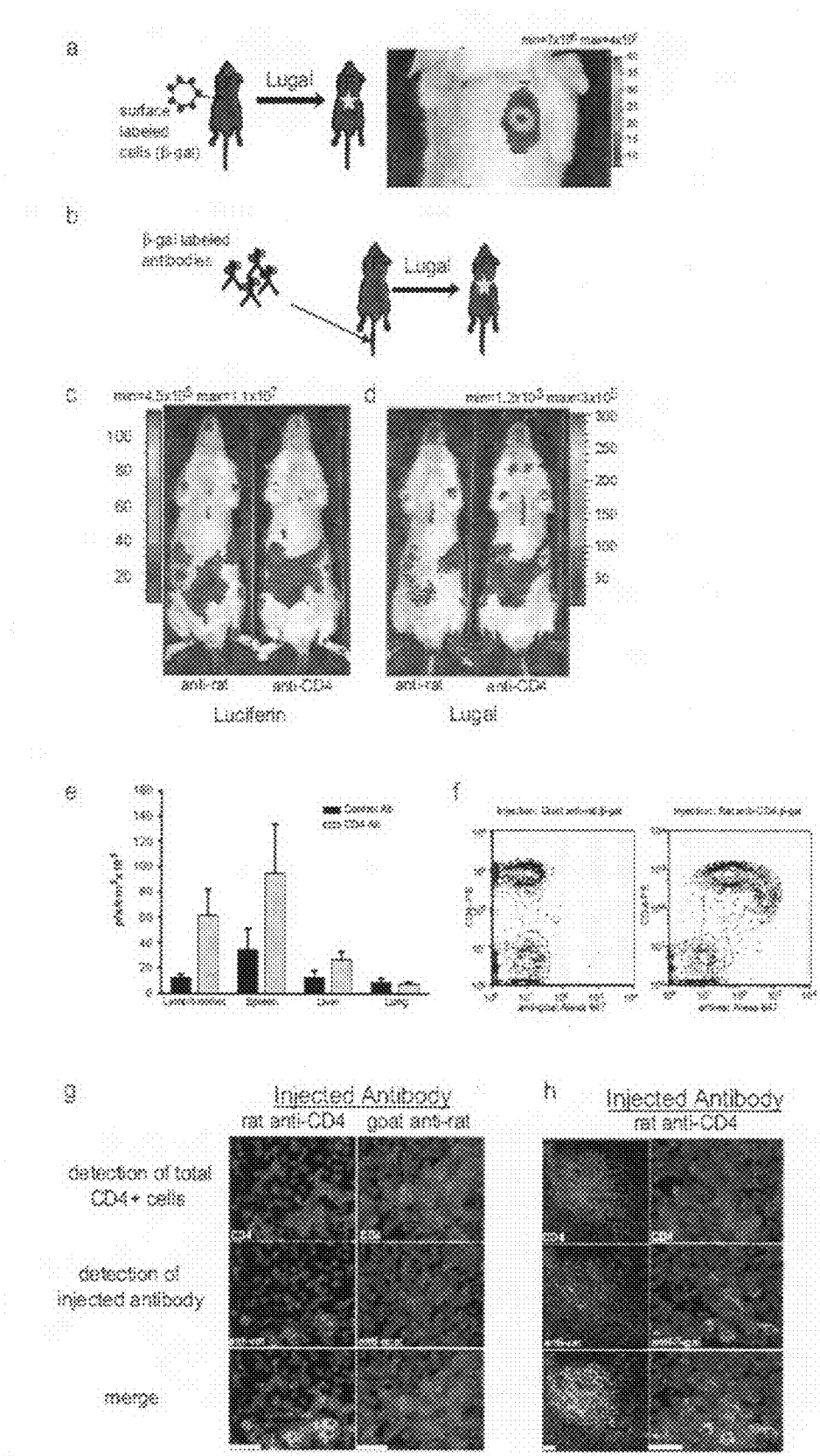
FIG. 4: Luminescent imaging of lymphocyte distribution in vivo using anti-CD4 antibodies labeled with β-gal. (a) Injected cells extracellularly labeled with the β-gal reporter enzyme can be imaged using SRL. Untransduced C2C12 myoblasts, not expressing FLuc, were labeled with biotin followed by avidin conjugated to β-gal and injected into a FLuc mouse. Lugal was injected 24 hours later and showed a robust, local signal at the site of implantation. (b-h) Detection of endogenous CD4+ T-cells by injection of anti-CD4 antibodies conjugated to β-gal. (c) As a control, the pattern of FLuc activity from the FLuc bone marrow transplanted mice was determined by Luciferin injection. Luminescence intensity and distribution was similar in both mice showing a slight enhancement over organs containing high densities of blood derived cells. (d) The following day the same mice were injected with an anti-CD4 antibody conjugated to β-gal or a control anti-rat antibody similarly labeled with β-gal. Four hours after antibody injection, Lugal was injected intraperitoneally, revealing markedly different antibody distributions in both mice. A clear luminescent signal was seen in the cervical lymph nodes and the spleen of the mouse injected with the CD4 antibody (arrows, right panel), whereas only weak regional luminescence was seen in the mouse having received the control antibody (left panel). Bioluminescent images are quantified in photons/sec/cm$^2$. (e) Quantification of luminescence after Lugal injection in regions of CD4+ T-cell enrichment. No difference was observed between the animals over the right thorax, an area containing relatively few blood cells. However, the signal over the liver was slightly enhanced in the mouse injected with the anti-CD4 antibody. A 3 to 5-fold higher signal was seen over the spleen and both cervical lymph nodes of the mouse injected with the anti-CD4 antibody in comparison to the control, highlighting the organs containing high densities of CD4 lymphocytes. (f) Flow cytometry of peripheral blood confirms the specificity of in vivo labeling of CD4-lymphocytes. Detection of the cells bound by the injected antibody was performed using Alexa 647 labeled secondary antibodies, and total CD4 expression was determined using a PE labeled primary antibody. Thus CD4+ cells that were bound by the injected antibody will be positive for both markers. None of the CD4+ cells from the control mouse were double positive whereas a significant proportion of the CD4+ cells from the mouse injected with the CD4 antibody were strongly double positive. (g) To detect lymphocytes labeled by the injected antibody in tissue, cryosections from spleens harvested 4 hours after intravenous injection were co-stained using Alexa 546 labeled secondary antibodies against the injected antibody (green) and APC labeled primary antibodies to CD4 (red). Clear membrane staining was obtained by the secondary antibody to the injected rat-anti-CD4 antibody (left panels). All cells positive for the injected antibody also co-stained for CD4, showing that cell targeting by the injected antibody was specific. Injection of the control antibody showed no significant signal in the regions of high lymphocyte density in the spleen (right panels). Scale bar is 15 μm. (h) The cells positive for the injected CD4 antibody colocalized with total CD4 positive cells around central arterioles (left panels, scale bar 50 μm). The antibody-β-gal conjugate remained intact and could be colocalized at the cellular level with total CD4 staining using an anti-β-gal antibody (right panels, scale bar 15 μm).

For the experiment shown in FIG. 4a, the surface of wild type C2C12 cells not expressing LacZ or FLuc was covalently labeled with 10 mM Sulfo-NHS-Biotin for 30 min (Pierce) and incubated with avidin-β-gal for 1 hour (Vectorlabs), washed 3× in PBS/BSA and $5\times10^5$ cells were implanted subcutaneously into the back of FLuc mice. Lugal was injected intraperitoneally 24 hours after cell implantation. For experiment shown in FIG. 5, C2C12 cells expressing FLuc-IRES-lyt2 were incubated for 1 hour with monoclonal rat-anti-lyt2 (1:500) antibody (BD Pharmingen), washed twice and $10^6$ cells were injected into the right TA of a BALB/c nude mouse, whereas the same cells without antibody preincubation were injected into the left TA. One hour after cell implantation, β-gal-labeled anti-rat antibodies (~20 ug) (β-galactosidase-labeled anti-rat antibody, Southern Biotech) were injected intravenously in order to target the localization of pre-labeled cells, and Lugal was injected intraperitoneally 4 hours later. The experiment shown in FIG. 3 was performed on FVB mice transplanted with bone marrow from FLuc mice. Three months after bone marrow transplantation, baseline luminescence was determined by luciferin injection. β-gal-labeled anti-CD4 antibodies were injected intravenously via the tail vein in one group of mice, whereas 1 ug of control antibody was injected into a second group of mice, (n=2/group). Imaging of β-gal activity was performed by intraperitoneal injection of Lugal.

F. Histology, Histochemistry and Immunofluorescent Staining of Tissue Samples

Organs from FVB mice were harvested 4 hours after injection of anti-CD4 or control antibodies, embedded in OCT and snap-frozen in freezing methylbutane. For immunofluorescent staining, 10 μm cryosections were fixed in 1.6% formaldehyde, and blocked using 2% normal goat serum, 0.5% casein and 0.3% Triton-X-100 (1 hour). Slides were incubated (1 hour) with APC-labeled rat monoclonal antibody against CD4 or TCR-β (BD Biosciences). To identify the fraction of lymphocytes labeled by the intravenously injected rat-anti-CD4 or goat-anti-rat antibodies, cryosections were co-stained using Alexa 546 labeled anti-rat or anti-goat antibodies respectively (Molecular Probes/Invitrogen). Hoechst-33258 was used to stain nuclei. Slides were analyzed using a Zeiss Axioplan microscope. TA muscle samples were obtained from Myf5nLacZ mice 4 days after notexin injection. Cryosections were fixed in paraformaldehyde as described and stained for H&E or X-Gal.

G. Near-Infrared Fluorescent Imaging of β-Gal Activity

Near infrared fluorescent imaging of β-gal activity was performed as previously described (Tung, C. H. et al. (2004) In vivo imaging of beta-galactosidase activity using far red fluorescent switch. Cancer Res. 64:1579-83). The near-infrared imaging probe DDAOG (Molecular Probes) was injected intravenously (0.5 mg of DDAOG in 100 μl of DMSO and PBS (1:1)). NIRF reflectance imaging was performed using an IVIS-200 imager (Xenogen) with a custom filter set (excitation: 615-645; emission: 680-720 nm) (Omega Optical). Images were continuously acquired over 45 min after substrate injection and the images showing optimal signal-to-noise ratios were chosen for comparison.

II. Results

A. Luminescent Imaging of Genetically Engineered Cells Injected into Mice

To test whether the substrate, Lugal, could cross the plasma membrane and enter live cells, we engineered C2C12 myoblasts to express either FLuc alone (FLuc cells) or together with β-gal (FLuc/LacZ cells). The cell lines were plated in a 384-well dish and luminescence was measured after addition of Lugal to the medium. The FLuc/LacZ cells generated strong luminescent signals at Lugal concentrations as low as 10 μg/ml whereas the FLuc cells failed to generate a measurable signal except at the highest Lugal concentration (1000 μg/ml). The luminescence was proportional to substrate concentration and cell number (FIG. 1b). The membrane permeability of Lugal was compared to luciferin on intact cells and cell lysates (Fluc/LacZ and Fluc cells, respectively). Both substrates showed a progressive gain in signal as increasing concentrations were applied to intact cells (FIG. 1c). The lysates showed a higher luminescence signal than intact cells using either substrate. Overall, the signal generated from intact Fluc/LacZ cells in the presence of Lugal was about one fourth of that obtained with luciferin (FIG. 1d). Lugal was well tolerated by the cells which exhibited no signs of toxicity after prolonged exposure to the substrate even at the highest concentrations used. These results demonstrate that Lugal can cross the membrane of intact mammalian cells and provide a live cell measurement of β-galactosidase activity by luminescence.

To demonstrate that Lugal can be used non-invasively to detect LacZ expressing cells in live animals, $1\times10^6$ FLuc/LacZ cells were injected into the tibialis anterior (TA) muscle of the right leg and an equivalent number of FLuc cells were injected into the left TA of live mice (FIG. 1e, diagram). The in vivo bioluminescence profile obtained after intraperitoneal Lugal injection revealed a 30 to 200-fold greater signal in the right than in the left leg (FIG. 1e, left data panel). When the same animals were injected 24 hours later with luciferin, the bioluminescence profile was similar for both injection sites, demonstrating that implantation of both cell types was successful (FIG. 1e, right data panel). In addition, these data show that Lugal does not require intravenous administration, as it is absorbed following intraperitoneal injection which is a simpler technique to perform, making it possible to image β-gal-expressing cells rapidly in several live mice simultaneously.

Figure 5:
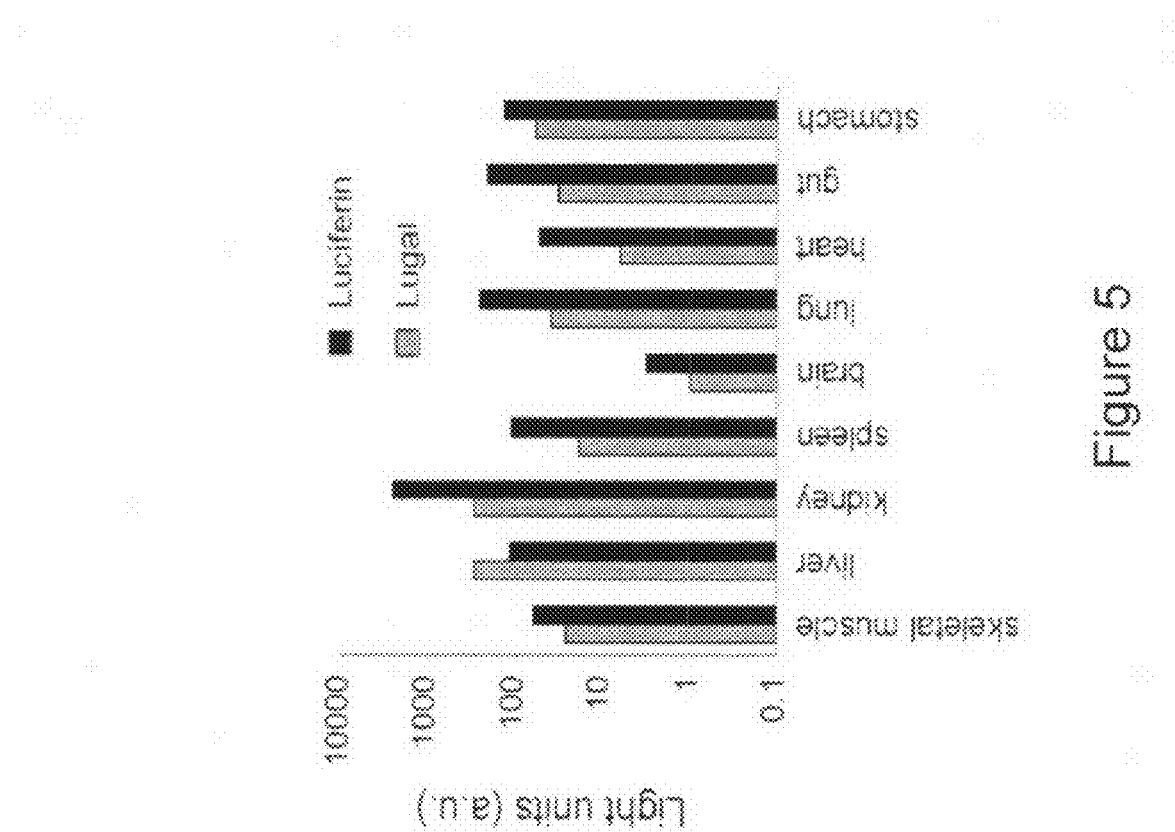
FIG. 5: Lugal and luciferin show biodistribution to major organs following intraperitoneal injection in 2 separate mice. Twenty minutes after injection of the indicated substrate, mice were anesthetized and perfused. Indicated organs were harvested, snap frozen, homogenized, and active substrate was determined by simultaneous addition of β-gal and FLuc enzymes. The biodistribution patterns of both substrates are similar, showing predominant distribution to the liver, kidneys, and lung with weak penetration into the brain tissue.
Figure 6:
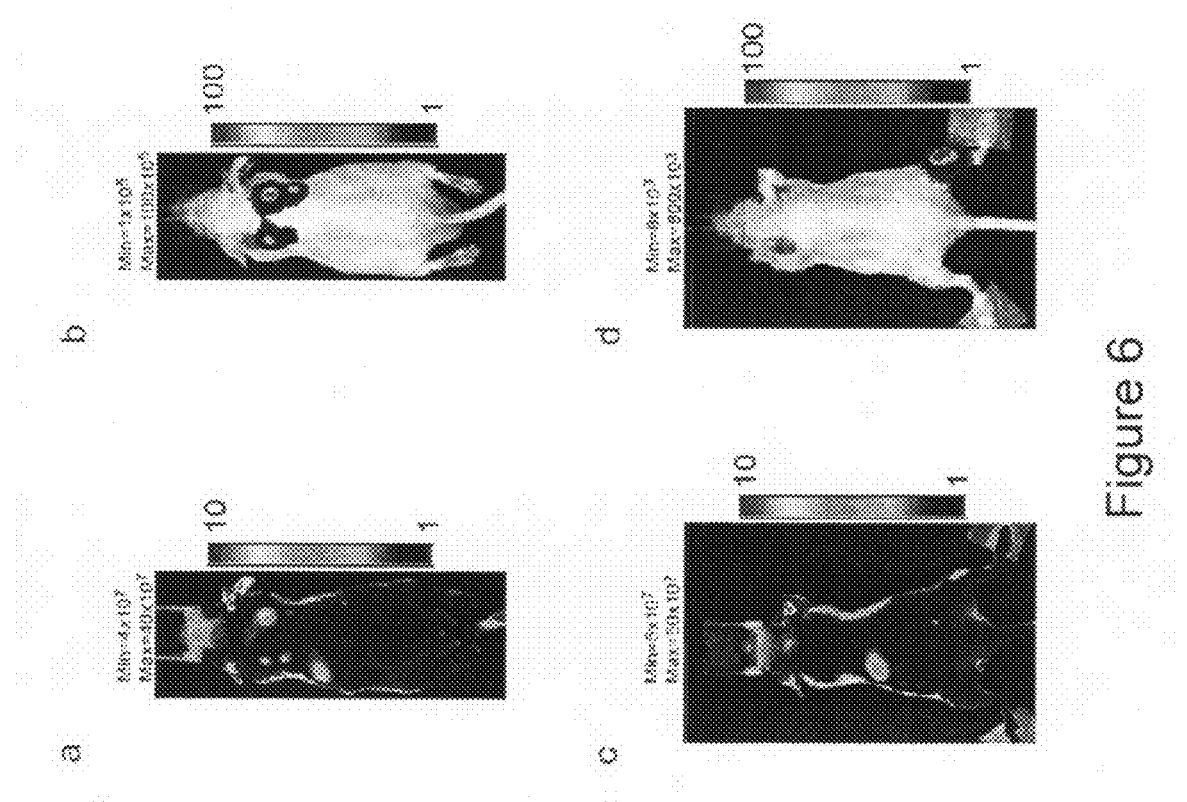
FIG. 6: Comparison of bioluminescent and fluorescent imaging of β-gal activity. (a and b) Mice were implanted subcutaneously with cells expressing LacZ and FLuc with cell numbers ranging from $2 \times 10^5$ to $2 \times 10^6$. (a) Fluorescence imaging using DDAOG revealed the implantation sites with signal-to-noise ratios after background substraction of 1.4 to 3.4-fold. (b) By comparison, the corresponding signal-to-noise ratios were 36- to 235-fold using Lugal (c and d). Both methods were compared in leg muscles as an example of deeper tissues following implantation of 1×10⁶ cells expressing either FLuc alone (left leg) or LacZ and FLuc (right leg). (c) Fluorescence imaging revealed a 2.8-fold signal-to-noise ratio (right vs. left leg). (d) Using Lugal, 429-fold signal-to-noise ratio in luminescence was obtained (right vs. left leg). Scales are arbitrary units for better comparison (ranges 1-10 for fluorescent and 1-100 for luminescent images). Minimum and maximum ranges for the scale bars shown are expressed in photons/s/cm² above each image.

To ensure that Lugal penetrates different organs similarly to luciferin, we measured the tissue distribution of both substrates. Animals were injected i.p. with either luciferin or Lugal. Twenty minutes after injection the animals were perfused and the organs isolated. Each tissue was lysed separately and luminescence was measured in a 96-well dish after addition of both recombinant β-gal and FLuc in the appropriate assay buffer. Although the luminescence from the luciferin injection was generally higher, the two substrates share similar distribution patterns (FIG. 5). A comparison between Lugal bioluminescence imaging and the fluorescent method for in vivo imaging of β-gal-activity using 7-hydroxy-9H-(1,3-dichloro-9,9-dimethylacridin-2-one) β-D-galactoside, DDAOG (Tung, C. H. et al. (2004) In vivo imaging of beta-galactosidase activity using far red fluorescent switch. Cancer Res. 64:1579-83), showed a 30- to 60-fold higher signal-to-noise ratio using Lugal in subcutaneous tissues, and a 150-fold higher signal-to-noise ratio in deeper tissues (skeletal muscle) (FIG. 6). The results from the DDAOG imaging were obtained using an optimized filter set and background subtraction according to the published technique (Tung, C. H. et al., supra). The use of spectral imagers such as the CRI maestro imaging system may be able to further increase the sensitivity of this method.

Figure 2:
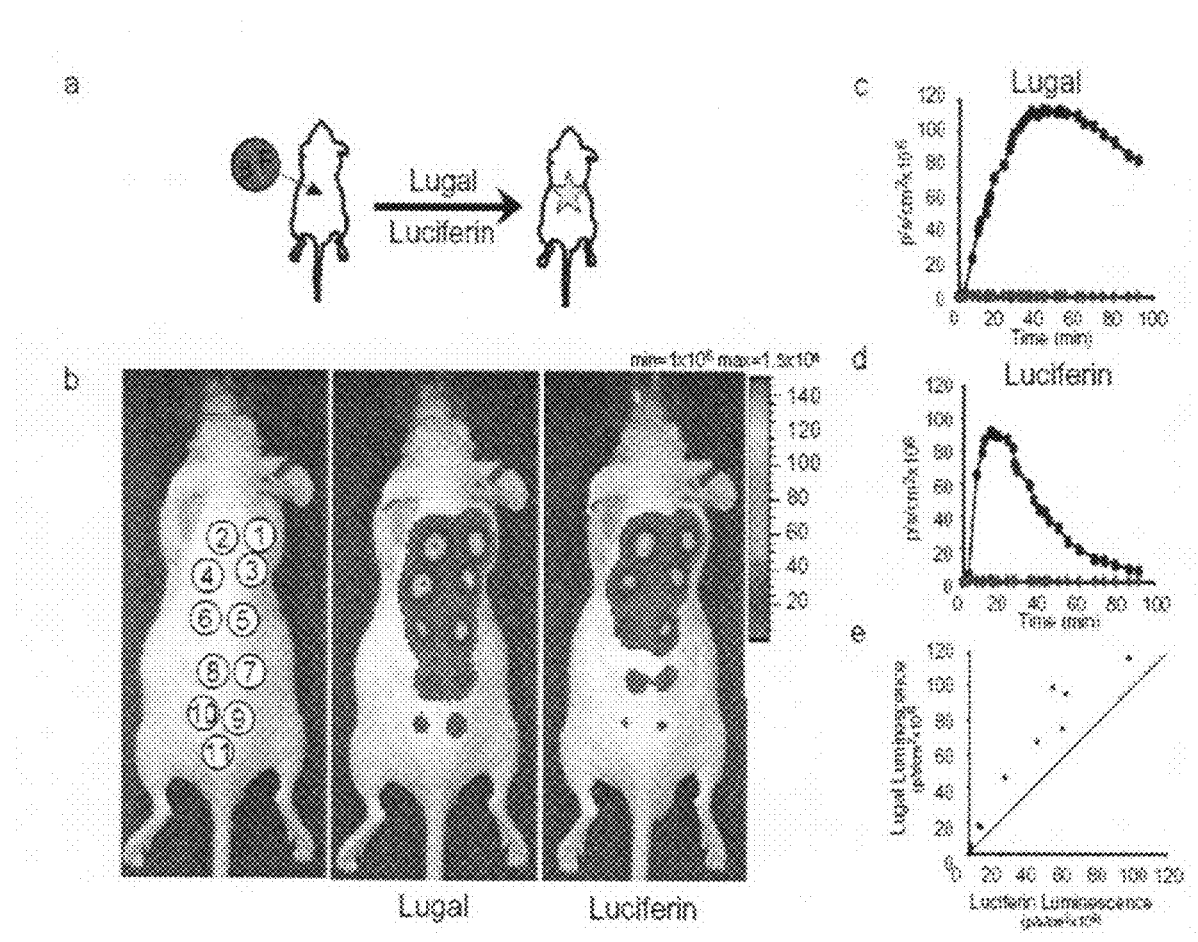
FIG. 2: Sensitive and quantitative bioluminescent imaging of β-gal activity in living mice using Lugal. (a) To determine the correlation between Lugal and luciferin generated luminescence serial dilutions of FLuc/LacZ cells were implanted subcutaneously into the back of a BALB/c nude mouse and imaged using either luciferin or Lugal. (b) The cell numbers corresponding to the implantation sites are as follows: 1) $2 \times 10^6$; 2) $1.5 \times 10^6$; 3) $1 \times 10^6$; 4) $7.5 \times 10^5$; 5) $5 \times 10^5$; 6) $2.5 \times 10^5$; 7) $2 \times 10^5$; 8) $1.5 \times 10^5$; 9) $1 \times 10^5$; 10) $5 \times 10^4$; and spot 11 served as the background reference (b, left panel). Lugal was administered intraperitoneally 6 hours after implantation and bioluminescence imaging shows that all sites are clearly visible (b, middle panel). Similarly all implantation sites provided signals above background when imaged 6 hours later using an equimolar dose of luciferin (b, right panel). Bioluminescent images are quantified in photons/sec/cm$^2$. (c-e) The time course of light emission from the implantation site containing $1.5 \times 10^6$ cells was quantified after Lugal or luciferin injection (black curve). Background signal from spot 11 is plotted as a reference (red curve). Following Lugal treatment, the light emission peaked at approximately 35 min for Lugal (c) and 15 min. for luciferin (d). The peak luminescence signal from each implantation site after Lugal treatment was analyzed versus the peak luminescence from luciferase injection (e) showing a good correlation between both substrates. The line indicates an ideal correlation between both signals. The results are representative of 5 independent experiments. Bioluminescent images are quantified in photons/sec/cm$^2$.

Experiments were designed to determine the linearity and sensitivity in vivo of the two-step SRL assay using the Lugal substrate compared with the widely used FLuc assay using the luciferin substrate. Different numbers of FLuc/LacZ cells, ranging from $5 \times 10^4$ to $2 \times 10^6$, were implanted subcutaneously in 10 different locations into a wildtype mouse and imaged 6 and 12 hours later by injection of Lugal or luciferin, respectively (FIG. 2a). To permit comparison of the two substrates, both were intraperitoneally injected at 0.5 μmole/kg based on the optimal dose routinely used for in vivo imaging of FLuc. Using either substrate, all implantation sites were readily visible above background (FIG. 2a). Due to the high luminescent signal obtained from the sites injected with the greatest number of cells, a short five-second exposure was used to avoid saturation and preserve linearity. The time course of luminescence differed, with the luciferin signal peaking at approximately 15 minutes and declining rapidly relative to the Lugal signal which peaked at approximately 35 min and declined gradually over the subsequent four hours (FIGS. 2c and d). Quantification of peak luminescence obtained from each implantation site showed a highly significant correlation between luciferin and Lugal luminescence, with similar low detection limits and dose responses over a 50-fold range (FIG. 2e). These results show that the SRL in vivo imaging of β-gal generates quantitative signals on a par with those obtained using the established FLuc/luciferin system. Thus, β-gal can be effectively imaged in vivo when used in conjunction with FLuc.

B. Luminescent Imaging of Inducible β-Gal Expression in Transgenic Mice

A bioluminescent model of muscle regeneration was generated by crossing mice expressing a nuclear LacZ under the control of the Myf5 promoter (Tajbakhsh et al., supra) with mice ubiquitously expressing FLuc under the control of the β-actin promoter (Cao et al., supra). Myf5 is a transcription factor that plays a role in muscle specification during development. In the adult mouse, Myf5 expression is specifically induced in damaged muscle tissue undergoing regeneration (Cooper, R. N. et al. In vivo satellite cell activation via Myf5 and MyoD in regenerating mouse skeletal muscle. J Cell Sci 112 (Pt 17), 2895-901 (1999)). Mice heterozygous for the Myf5nLacZ transgene were mated with homozygous FLuc mice (FIG. 3a). The F1 progeny harboring both the Myf5nLacz transgene and FLuc were used for analysis and the Myf5nLacZ–/FLuc+ littermates were used as controls.

Muscle damage and subsequent muscle regeneration were induced by injection of the snake venom toxin, notexin, which permeabilizes and destroys myofibers. Baseline luminescence was obtained prior to notexin injection by intraperitoneal administration of Lugal. Notexin was injected into the TA of the left leg of Myf5nLacZ+/FLuc+ mice or Myf5nLacZ–/FLuc+ control mice. In the Myf5nLacZ–/FLuc+ mice injected with notexin, no increase in luminescence was detected at any time point. By contrast the injured leg of the Myf5nLacz+ mice began to increase in luminescence 24 hours after notexin injection by comparison with the contralateral uninjured leg. Between 3 to 5 days after notexin treatment, the signal peaked, began to decline at 7 days, and returned to baseline between 11 and 15 days, at which point the treated and untreated legs were indistinguishable (FIG. 3b). Quantification of luminescence emission over time showed a 2-fold increase in signal from the injured leg of the Myf5nLacZ+/FLuc+ mice in comparison with the untreated leg (FIG. 3c). Histochemical analysis of tissue sections at the peak, day 4 post notexin, are shown in comparison to controls using the chromogenic β-gal substrate X-gal, revealing a marked increase in β-gal activity localized to the nucleus of activated myoblasts (FIG. 3d). This time course of muscle regeneration is similar to the previously published Myf5 expression profile in regenerating muscle following damage (Cooper et al., supra; Mendler, L., Zador, E., Dux, L. & Wuytack, F. mRNA levels of myogenic regulatory factors in rat slow and fast muscles regenerating from notexin-induced necrosis. Neuromuscul Disord 8, 533-41 (1998)). These data show that the same transgenic β-gal expressing mice can be used for classical histochemical staining as well as for non-invasive in vivo imaging over time using SRL.

C. Luminescent Imaging of Lymphocyte Distribution with Antibodies Conjugated to β-Gal To test whether extracellular β-gal activity could be imaged using Lugal, cells were covalently labeled with biotin on the plasma membrane, and then treated with an avidin-β-gal conjugate. A total of $5 \times 10^5$ labeled cells were injected subcutaneously into a transgenic FLuc mouse. A strong, localized luminescent signal was readily apparent in the area of injection that persisted for at least 24 hours (FIG. 4a). These results demonstrate that the luciferin generated by the cleavage of Lugal enters nearby cells providing a spatially resolvable luminescent signal. Thus, extracellular β-gal activity is locally detectable using Lugal.

Figure 7:
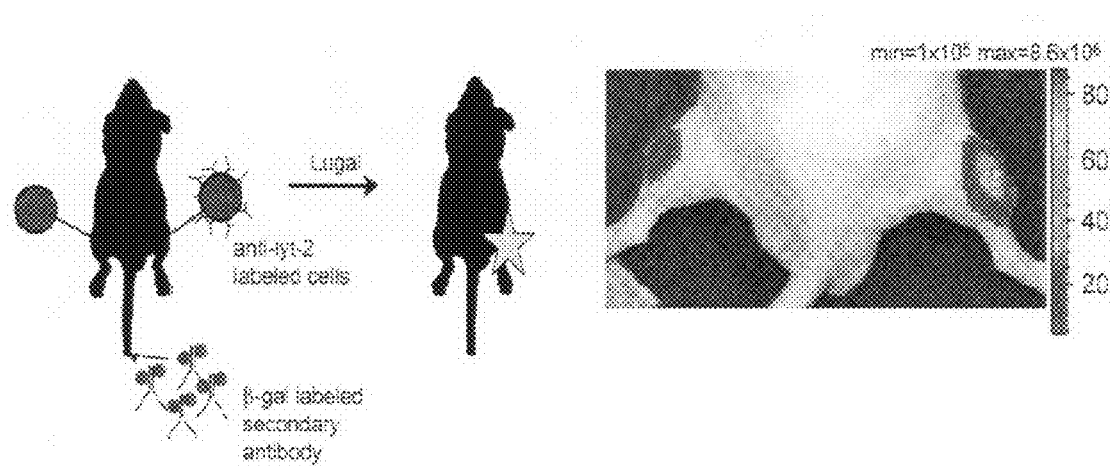
FIG. 7: Luminescent imaging of β-gal labeled antibodies. C2C12 cells expressing FLuc and lyt-2 were labeled in vitro with a rat anti-lyt-2 antibody, or left unstained. 1×10⁶ labeled cells were injected into the right TA, an equivalent number of unstained cells were injected into the left. An anti-rat antibody conjugated to β-gal was injected into the tail vein and Lugal was administered 4 hours later. The cells labeled with the primary antibody (right leg) induced a 3.7 fold higher luminescent signal indicating the injected antibody preferentially bound to the labeled cells. Bioluminescent images are quantified in photons/sec/cm².

Since extracellular β-gal could readily be imaged, we tested whether in vivo labeling of endogenous cell surface antigens might be feasible using antibodies conjugated to β-gal. As an initial test, FLuc expressing cells engineered to express lyt-2 (murine CD8) were incubated with an anti-Lyt-2 rat monoclonal antibody, and then injected into the right TA. As a control, the same cells that were not exposed to antibody were injected into the left TA. An anti-rat secondary antibody that had been covalently conjugated to β-gal was then delivered intravenously. Four hours later, mice were injected intraperitoneally with Lugal and imaged. The cells pre-incubated with anti-Lyt2 antibody prior to injection (right leg) exhibited 3.7-fold greater luminescence than controls (left leg) (FIG. 7). These results demonstrate that systemic administration of a β-gal labeled antibody can be used to selectively label cells in vivo and provide a non-invasive measure of cell location.

We then determined whether β-gal labeled antibodies could be used to localize endogenous cells by detecting physiologically expressed cell surface antigens. For this purpose, a rat antibody specific to the murine T-lymphocyte membrane protein, CD4, was covalently conjugated to β-gal. The β-gal conjugated goat anti-rat antibody used previously to detect the lyt-2 labeled cells served as the negative control (FIG. 4c). In order to facilitate identification of immune cells, bone marrow from FLuc mice was transplanted into lethally irradiated syngeneic recipients so that the blood derived cells expressed FLuc. Luminescence resulting from luciferin injection was obtained for each animal 24 hours prior to antibody injection to ensure that luminescence resulting from FLuc bone marrow engraftment was similar (FIG. 4c). To allow a quantitative comparison of the two antibodies, the CD4-β-gal antibody and control β-gal labeled antibody were each assayed for β-gal activity in vitro and amounts of antibody with equivalent enzyme activities were injected intravenously. The mice injected with the CD4 antibody exhibited strong luminescent signals from the cervical lymph nodes and spleen, whereas the mice injected with the control antibody had only weak luminescence from the spleen and the signal from the lymph nodes was not distinguishable from background (FIG. 4d). Quantification of the photon emission showed a three-fold increase in luminescence from the cervical lymph nodes and spleen of the anti-CD4 injected mice compared with the controls. No increase in signal was seen over the lung and a small increase was seen over the liver, an organ rich in blood cells but without specific abundance of lymphocytes (FIG. 4e). Previous studies using radioactively labeled anti-CD4 antibodies (Rubin, R. H., Baltimore, D., Chen, B. K., Wilkinson, R. A. & Fischman, A. J. In vivo tissue distribution of CD4 lymphocytes in mice determined by radioimmunoscintigraphy with an 111 In-labeled anti-CD4 monoclonal antibody. Proc Natl Acad Sci USA 93, 7460-3 (1996)) support the observed CD4+ T-cell enrichment in these areas.

Figure 8:
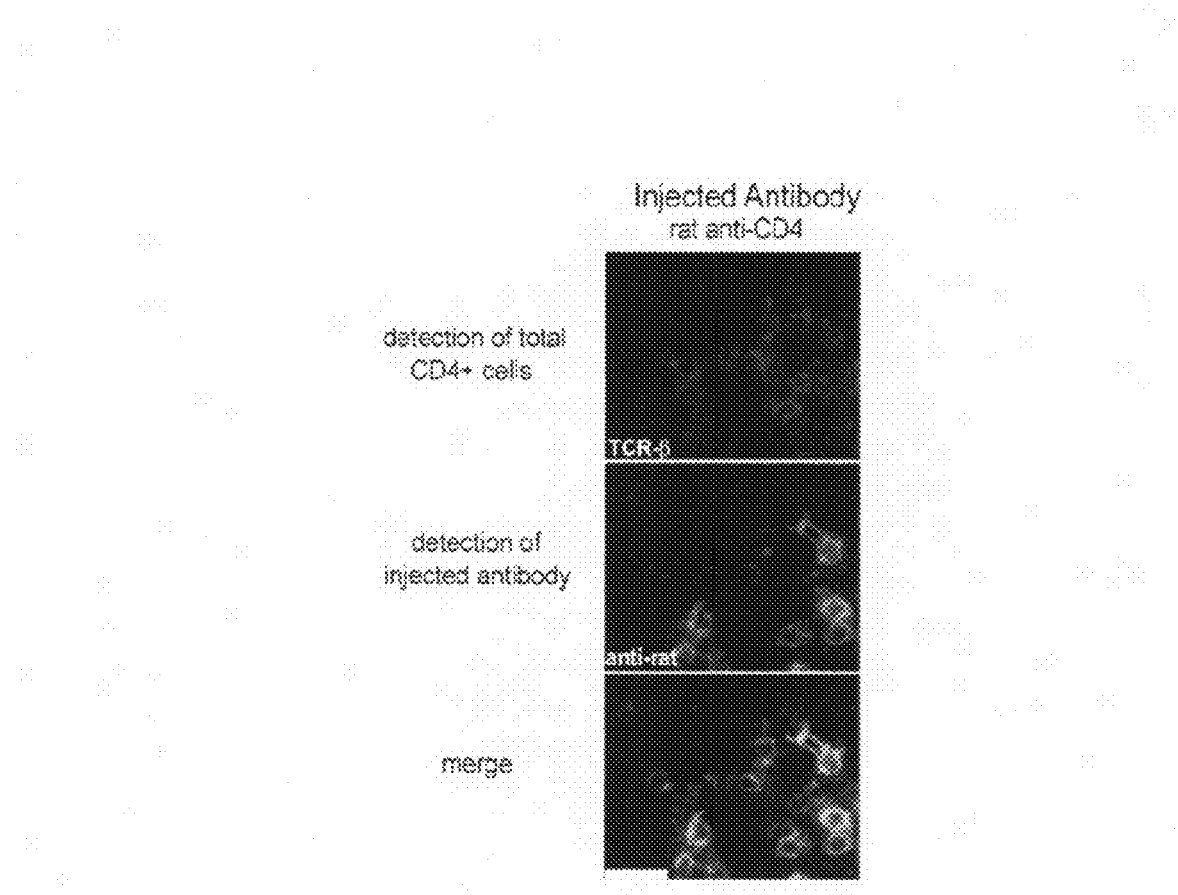
FIG. 8: Colocalization of injected anti-CD4 antibody with TCR-β chain. Splenic sections from the mouse injected with the anti-CD4-β-gal antibody were stained with an anti-rat antibody to detect the injected antibody (green), and an anti-TCR-β to detect total T-cells (red). Sections show distinct colocalization of the injected antibody with a subset of the TCR-β positive cells confirming that the injected CD4 antibody specifically stains T-lymphocytes.

To determine whether the anti-CD4 antibody specifically labeled CD4+ lymphocytes in vivo, we injected the same anti-CD4 and control antibodies intravenously into separate wild type mice and harvested the peripheral blood and tissue samples after 4 hours. Peripheral blood samples were stained with an anti-rat antibody labeled with Alexa 647 to detect the injected CD4 antibody, followed by the same CD4 antibody clone but conjugated to phycoerythrin (PE) to enable detection of the dual-labeled cells. Flow cytometric analysis showed that a majority of the CD4+ cells were clearly labeled with the injected antibody whereas no significant staining of CD4+ cells was detected using the anti-goat antibody in the control sample (FIG. 4f). Notably, the cells most strongly stained for the injected antibody showed decreased staining with the CD4 antibody indicating that some blocking of the epitope had occurred. These results show that the β-gal conjugated CD4-antibody specifically labels CD4+ T-cells in the peripheral blood. To determine the level of specific staining in the target tissues, we analyzed tissue sections from the spleen of both antibody injected mice by immunofluorescence. Spleens from each mouse were sectioned and stained with a CD4 antibody (red) to label the CD4+ T-cells, or an antibody specific to the injected antibody (green). The spleen from the mouse injected with the anti-CD4 antibody showed that the injected antibody specifically colocalized with a proportion of the CD4 positive cells, whereas no specific staining of the injected control antibody was observed (FIG. 4g). The staining in the spleen of the CD4 antibody injected mouse showed characteristic clustering around major arterioles (FIG. 4h, left panels) and colocalized with another T-cell marker, TCR-β (FIG. 8). Similar to the FACS analysis, the cells most strongly positive for the injected antibody were often weakly stained by the CD4 antibody. These results show that the injected CD4 antibody selectively labels CD4 expressing lymphocytes. To ensure these antibodies remained conjugated to the recombinant β-gal enzyme, sections were stained with an anti-β-gal antibody. The β-gal stained cells showed the same pattern of localization as those stained with the anti-rat antibody indicating the antibody-enzyme conjugate remained intact and was able to specifically label host cells.

These data show that intravenously injected CD4 antibodies conjugated to β-gal were able to specifically label cells within tissues. Thus β-gal labeled antibodies can be used to identify endogenous cells using non-invasive luminescent imaging, as well as cellular detection by flow cytometry and immunofluorescence analysis.

C. Discussion

The above results show that by coupling the exceptional luminescence properties of the FLuc enzyme to the well characterized and highly versatile β-gal enzyme, we generated a novel imaging approach that exploits the advantages of each enzyme. For FLuc, the substrate, luciferin allows highly sensitive in vivo luminescent imaging over time. For β-gal, there are multiple substrates that facilitate histochemical as well as quantitative fluorescent and flow cytometric analyses of β-gal expressing cells, but not luminescent imaging. Here we show that by coupling the activity of these two enzymes, the advantages of both can be realized in the same cells and mice, greatly extending the applications of bioluminescent imaging. It is believed that, in operation, Lugal is first cleaved by β-gal to generate luciferin, which is then cleaved by FLuc to produce light. Recently a peptide-luciferin conjugate was used for in vivo imaging of endogenous caspase activity however the toxicity and high dose of the compound used required the animal to be sacrificed shortly after injection (Shah, K., Tung, C. H., Breakefield, X. O. & Weissleder, R. In vivo imaging of S-TRAIL-mediated tumor regression and apoptosis. Mol Ther 11, 926-31 (2005)). By contrast our results show the Lugal substrate to be non-toxic similar to luciferin, and enable daily luminescent imaging over the course of at least two weeks without weight loss or other ill effects. We predict that the coupled reporter enzyme approach described here for β-gal can be applied to other commonly used reporter enzymes using substrates similar to Lugal.

SRL using Lugal constitutes the first luminescent measure of β-gal activity in live cells and animals. This was made possible because Lugal is cell permeable in tissue culture cells and mice. In vivo using Lugal, cells expressing β-gal and FLuc are 30-200-fold brighter than cells expressing only FLuc. These cells were detectable over a wide range of cell numbers with sensitivity on a par with luciferin allowing quantification by luminescence. Most fluorescent and radio-labelled substrates, as well as coelenterazine, the *renilla* luciferase substrate, require intravenous injection, which is a technically challenging and time consuming procedure. By contrast, Lugal, like luciferin, is systemically distributed following intraperitoneal delivery, enabling simultaneous imaging of large numbers of mice.

LacZ is historically the most commonly used reporter of gene expression in transgenic animals. The bacterial enzyme is stable in mammalian cells and survives standard tissue fixation protocols allowing histochemical visualization in tissue sections. Here we show that bioluminescent animal models can be rapidly derived from β-gal transgenics by mating them with FLuc mice. Using the F1 progeny of the Myf5/lacZ and FLuc transgenic mice, we generated a directly applicable bioluminescent model of muscle regeneration. Notexin induced damage to the muscle led to transient upregulation of the promoter of the transcription factor, myf5, in activated myoblasts in regenerating muscle. The resulting β-gal expression could be imaged non-invasively in longitudinal studies using Lugal, in conjunction with classical histochemical analyses of the same reporter gene in tissue sections. This study illustrates that bioluminescent mouse models can be effectively constructed from existing, thoroughly characterized, β-gal transgenic strains, obviating the need to re-create and re-characterize all strains with a FLuc transgene.

SRL using Lugal provides a means of imaging molecules covalently linked to β-gal in the interstitial and extracellular space. This is possible because β-gal, unlike FLuc, is active outside cells, as it does not require cofactors. In addition β-gal retains activity after harsh chemical treatment allowing it to be chemically linked to a wide variety of chemical and biological molecules. We show with two different examples that recombinant β-gal can be conjugated to antibodies and used to image cells within tissues upon administration of Lugal in live mice. Thus, cells can be directly labeled with a bioluminescent marker, β-gal, without genetic modification, selection, or in vitro culture, which could alter their ability to migrate or implant properly. Although a background activity is detected when Lugal is injected into FLuc transgenic mice, the signal from cells labeled with β-gal is significantly higher. Thus the imaging method described here provides the first bioluminescent alternative to fluorescent or radiological methods of in vivo cell labeling. We show that recombinant β-gal enzyme can be used to label probes in addition to antibodies such as molecules, drugs or hormones that could be tracked and quantified by luminescence in live animals.

We describe a novel bioluminescent imaging approach in which two enzyme activities are coupled such that the reporter enzyme cleaves a pro-substrate to release the substrate required by FLuc. This approach facilitates imaging of enzymes such as β-gal that could not otherwise be visualized by luminescence in live animals in vivo. This methodology greatly extends current applications of in vivo bioluminescence imaging by harnessing the advantages of FLuc while circumventing many of its limitations. Moreover, the two enzymes can be used as a dual reporter system when two different substrates are given sequentially. If luciferin, which is metabolized only by the constitutively expressed FLuc, is administered first, the location and mass of cells can be imaged. Upon Lugal administration, the pattern of inducible gene expression can then be imaged as a function of β-gal activity in the same cells. Both measurements can be obtained repeatedly over time in live animals. Although the system described here utilizes β-gal, the concept of sequential reporter-enzyme luminescence (SRL) should be readily applicable to other commonly used enzymes.

D. Conclusion

We show for the first time that β-gal activity can be monitored by luminescence imaging in intact tissue culture cells and live animals. The in vivo dose response and sensitivity characteristic of β-gal imaging are comparable to the well established FLuc imaging system. Because Lugal is well tolerated and can be easily administered intraperitoneally, repeated and simultaneous measurement of several mice is possible; by contrast, many radiological markers, fluorescent substrates as well as the luminescent substrate of *Renilla* luciferase substrate, must be administered via tail vein injection. By simply crossing mice, one harboring a LacZ transgene under the control of a damage-inducible tissue-specific promoter and the other ubiquitously expressing FLuc, we generated a bioluminescent model of muscle regeneration. The time course of muscle repair was not only imaged non-invasively utilizing a bioluminescent read-out, but also characterized at the cellular level in tissue sections using the chromogenic X-gal substrate. These findings show that using SRL, the vast numbers of β-gal transgenics that have been created over the years can now be used in studies requiring in vivo molecular imaging. Another advantage of SRL imaging using β-gal is the potential to visualize enzyme activity in the interstitial space of animal tissues. We show that cells labeled extracellularly with the recombinant β-gal protein can be efficiently detected and spatially localized using Lugal, indicating that cells can be directly labeled with a luminescent marker in the absence of genetic modification. Extending this technology to endogenous cells, we injected β-gal labeled antibodies specific for murine T-cells into living mice. After Lugal injection, the sites of T-cell accumulation including the spleen and lymph nodes were readily visible, indicating that SRL imaging of β-gal activity can be used to track endogenous cells and antigens. In summary, SRL imaging using β-gal combines the versatility of the β-gal enzyme and the excellent luminescent properties of the FLuc-luciferin system to enable BLI applications that were previously not possible.

EXAMPLE II

I. Materials and Methods

A. Generation of VEGF164-Producing Myoblasts

Generation of VEGF164-producing myoblasts is done as previously described (Springer et al. (1998) Mol. Cell. 2:549-558). In brief, a retroviral vector construct encoding VEGF164 (pMFG-VEGF164) is transfected into Phoenix packaging cells (Pear et al., (1993) PNAS 90:8392-96) and retroviral supernatants (containing MFG-VEGF164 virus) are collected and frozen on dry ice. Primary myoblasts are transduced at high efficiency with four successive exposures to these MFG-VEGF164 viral supernatants to produce a population of VEGF164-producing myoblasts (see Springer and Blau (1997) Somat Cell Mol Genet. 23(3):203-9).

B. Assessment of Angiogenesis by VEGF164-Producing Myoblasts

The Tie-2 gene is expressed on vascular endothelial cells, and as such, its expression is upregulated upon induction of angiogenesis. To study the ability of VEGF164-producing myoblasts to induce angiogenesis, transgenic mice in which LacZ is under the control of the Tie-2 promoter (Tie-2-LacZ transgenic mice) are crossed with FLuc mice to produce double transgenic Tie-2-LacZ$^+$/FLuc$^+$ mice. In certain experiments, Tie-2-LacZ$^-$/FLuc+ littermates are employed as negative controls. Myoblasts expressing VEGF164 (as described above) or control myoblasts (non-infected or infected with empty retroviral vector) are implanted into the leg muscle of Tie-2-LacZ+/FLuc+ mice on day 0. Imaging is performed (as described in Example I, above) by intraperitoneal Lugal injection on 2 consecutive days prior to myoblast implantation, and 1, 3, 4, 5, 6, 7, 8, 9, 11 and 15 consecutive days thereafter. The sites of implantation for both VEGF164-expressing and control myoblasts are quantified in photons/$cm^2$/sec. For each measurement, a ratio is obtained from the site implanted with VEGF164-expressing myoblasts and the site implanted with control myoblasts and expressed as a % of the initial pre-treatment values.

II. Results

As demonstrated in Example I (above), Lugal can be used non-invasively to detect LacZ expressing cells in live animals. This finding is used to study the effect of VEGF164-producing myoblasts on angiogenesis when implanted into mice. VEGF164-producing myoblasts are propagated as previously described (Rando et al. (1994) J. Cell. Biol. 125: 1275-87), trypsinized, and implanted into the muscle of anesthetized mice (approximately $5\times10^5$ in 5 μl PBS per injection). Anesthesia consists of inhaled methoxyflurane (Mallinckrodt Veterinary, Mundelein, Ill.) throughout the procedure. Angiogenesis induced by the VEGF164-producing myoblasts is determined by observing the in vivo bioluminescence profile after intraperitoneal Lugal injection. Specifically, higher levels of bioluminescence at implantation sites of VEGF164-expressing myoblasts over control myoblasts indicates higher levels of angiogenesis at those sites. The induction of angiogenesis in this system is confirmed by tissue histochemical analyses.

EXAMPLE III

I. Materials and Methods

A. Plasmids and Reagents

The SSTR2 and AVPR2GPCR-α* fusions were created by PCR amplification from cDNA constructs obtained from the UMR cDNA resource center. AGTR1 was RT-PCR amplified from mouse RNA. The B2AR was derived from a retroviral construct. The entire coding sequence of the GPCR was included minus the stop codon. The PCR products were cloned into the Mfel-Xhol sites of the MFG-YFP-H31Rα-IRES CD8 plasmid to create the GPCR-α* retroviral fusions. The βarrestin2-ω construct was created by PCR amplification of the β-arrestin2 and inserted using the Mfel-Xhol sites of the pWZL-ω vector. Firefly Luciferase was cloned into the MFG-IRES-CD8 vector. The constitutively active Ras mutant was a generous gift from P. Khavari. Isoproterenol, [Arg$^8$]-vasopressin, angiotensin and somatostatin somatostatin-14 were obtained from Sigma.

B. Cell Line Creation

C2C12 cells were grown in DMEM with 20% FBS and pen/strep. For the in vitro experiments, C2C12 cells were transduced with the GPCR-α* and β-arrestin2 retroviral constructs. For the in vivo experiments cells were first transduced with the Ras and luciferase plasmids. Cells were sorted using flow cytometry for CD8 expression to ensure that all cells expressed luciferase. Cells were then transduced with the GPCRα* and βarrestin2 retroviral constructs. Retroviral transduction was accomplished by lipofectamine (Invitrogen) transfection of the ecotropic retroviral packaging cell line φnx cells (a generous gift from Garry Nolan). After 48 hours, the supernatant was applied to the target cells in the presence of 8 ug/ml polybrene. After a 15 min. incubation at 37° C. Cells were spun at 2,00 RPM for 30 min. then returned to a humidified 37° C. incubator.

C. β-Galactosidase Activity in Cells

Cells expressing the GPCR-α* and β-arrestin2-ω fusions were seeded at 20,000 cells/well in a 96-well dish overnight. Ligand was added for 1 hour. Media is aspirated and 50 ul of lysis solution (buffer A) and substrate (Gal-screen) in a 25:1 ratio was added to each well. The plates were incubated for 60-90 min at room temperature before reading in a TR717 luminometer with an integration time of 1 second. EC50 values were calculated using non-linear regression with a variable slope sigmoidal dose response algorithm in Prism software (Graphpad).

D. Bioluminescent Imaging in Mice

All protocols were approved by the Administrative Panel on Laboratory Animal Care at Stanford University School of Medicine. BALB/c nude were obtained from the Stanford University in-house colony. C2C12 myoblasts were harvested and suspended in 0.5% BSA in PBS at a final concentration of $10^8$ cells/ml for injection. $4\times10^6$ cells carrying the β2/arrestin β-gal/Ras/FLuc or the SSTR2/arrestin β-gal/Ras/FLuc constructs were subcutaneously into the back of mice (2 injections/mouse), and allowed to grow into small tumors over 7 to 14 days. To induce the β2AR cells, 6 mg/kg isoproterenol (Sigma-Aldrich) was injected i.p. 1 hour before Lugal injection and bioluminescent imaging. To test specific inhibition, Sotalol 3 mg/kg (Sigma-Aldrich) was injected i.p. 1 hour before isoproterenol injection, and Lugal injection and imaging was performed 1 hour after isoproterenol injection. To induce the SSTR2 cells, octreotide (0.3 μg/kg) was injected i.p. 1 hour before Lugal injection and bioluminescent imaging.

Imaging was carried out using a Xenogen-100 device as previously described. Briefly, the system is composed of a light-tight imaging chamber, a digital CCD camera colled by a cryogenic refrigeration unit and a computer system (Living Image™ 2.50 software, Xenogen, Alameda). Imaging of β-gal activity was done using a modification of our previously described method: Beta-Glo (Promega) was reconstituted in 1 ml $H_2O$ (1 vial luciferin to 1 ml $H_2O$); 15 ul was diluted to 150 ul PBS and injected i.p. and image was integrated over 120 to 180 sec. Images were serially acquired up to 1 hour and stored for subsequent off-line analysis, and images acquired 3 to 5 minutes after Lugal injection were used for analysis unless otherwise indicated.

II. Results

A. Design of the Arrestin Assay

Figure 9:
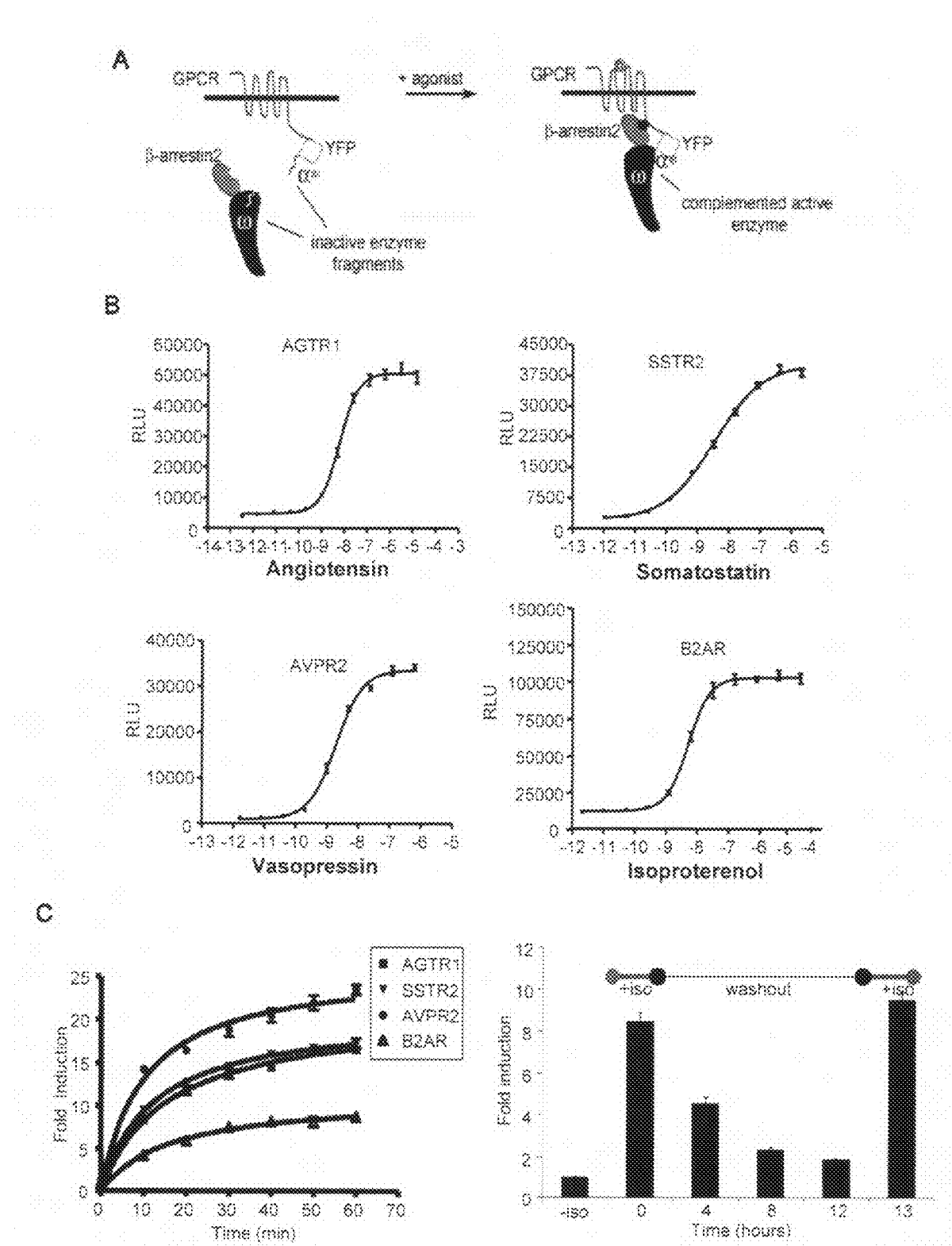
FIG. 9: GPCR activation assay. (A) The GPCR of interest is fused to YFP and the α* peptide while βarrestin2 is fused to the N-terminus of ω. Activation of the GPCR creates a binding site for arrest and forces the complementation of α* and ω. (B) C2C12 cells transduced with the βarrestin2-ω and the indicated GPCR-α* fusions were plated in 96-well dishes. The cells were treated with increasing doses of the appropriate ligand and β-galactosidase activity was measured using Gal-Screen, a homogeneous chemiluminescent assay system. (C) Time course of arrestin binding. Cells expressing the βarrestin2-ω and GPCR-α* fusions were treated with maximal doses of ligand for the indicated times and β-gal activity was measured as a measure of the GPCR-βarrestin2 interaction. β-gal complementation provides a measure of the dynamic interaction of βarrestin2 and GPCRs. Cells expressing the β2AR-α* and βarrestin2-ω were treated with 1 uM isoproterenol for 1 hour (time 0) then the ligand was removed by serial washes. β-gal activity was measured at regular intervals (4, 8, and 12 hours). The cells were then restimulated with isoproterenol and the increase in β-gal activity was measured. All values are expressed as a fold increase over the activity obtained from cells that have not been treated with ligand.

We have recently reported the generation of a β-galactosidase complementation system with high dissociation rates and, hence, weak complementation properties. Previously this approach has been successfully used in novel applications to monitor protein translocation and protein interactions in living mammalian cells. We sought to apply it to the interaction between different GPCRs and arrestin. The protein interaction detection system consists of a modified α"donor" peptide (α*) and the M15 "acceptor" of β-galactosidase (ω). Due to the deletion of amino acids 11-41, the M15 fragment is completely inactive. α* is a point mutant of the wild-type α peptide that has very little activity when co-expressed with the ω, as previously described (Wehrman et al., Enzymatic detection of protein translocation. Nature Methods, 2005 July; 2(7):521-7). When two proteins that interact are fused to the α* and ω fragments, the interaction of the proteins enhances the complementation resulting in readily detectable increases in β-galactosidase activity (Wehrman et al., A system for quantifying dynamic protein interactions defines a role for Herceptin in modulating ErbB2 interactions. Proc Natl Acad Sci USA. 2006 Dec. 12; 103(50):19063-8). The GPCR activation assay was designed to cause minimal perturbation of the receptor physiology by fusing the GPCR to the smaller of the two fragments, α*. Yellow fluorescent protein (YFP) was included in these constructs between the GPCR and α* to provide a sortable marker for the selection of cells containing the constructs. βArrestin2 was fused to the amino terminus of the ω fragment (FIG. 9a). Cells stably transduced to express combinations of these constructs are referred to from hereon as the GPCR/arrestin β-gal complementation system.

A cell-based system was generated by first transducing C2C12 myoblasts with the retroviral arresting construct, linked to the hygromycin resistance gene via an internal ribosome entry site (IRES), and selection of cells with 1 mg/ml hygromycin. The resulting parental cell line stably expressing the arresting fusion protein was then transduced with either of the following GPCR α* constructs: human somatostatin receptor 2 (SSTR2-α*), human β2 adrenergic receptor (β2AR-α*), mouse angiotensin receptor 1 (AGTR1-α*), or human vasopressin 2 receptor (AVPR2-α*). Cells were sorted by fluorescence-activated cell sorting (FACS) for expression of the GPCR construct using YFP as a marker. The sensitivity, specificity and time course of activation of the resulting cell lines carrying the panel of different GPCR-α* constructs and arrestin-ω were characterized and compared in vitro (see FIG. 9B and FIG. 9C, described below).

B. Measurement of GPCR Activation In Vitro

To test the sensitivity of the GPCR/arrestin assay, each cell line was plated in a 96-well dish and treated for 60 minutes with escalating doses of the indicated agonist (FIG. 9B). β-gal activity was measured using a luminescent substrate (Tropix). The AGTR1 and SSTR2 cell lines showed an increase in β-galactosidase activity of greater than 15 fold in response to the agonists. The EC50 values of angiotensin and somatostatin are in good agreement with radiolabeled ligand binding assays. The AVPR2 cell line exhibited the largest induction of enzyme activity with a maximum that was 25-fold the unstimulated value. The EC50 determined for vasopressin using the present method was in the expected range. Treatment of the β2AR cell line with isoproterenol resulted in an 8-fold increase in β-galactosidase activity with an EC50 of 8 nM.

The time course of activation did not differ significantly among the four receptors, as expected (FIG. 9C, left panel). Following removal of the inducer and subsequent washing, signal decrease was observed that returned to levels undistinguishable from baseline within 12 hours (FIG. 9C, right panel). Using β-galactosidase activity as a measure of arrestin binding, all cell lines were found to reach 80% of their maximum values within 30 min of agonist addition. Incubation times of up to two hours can be used to further increase the signal (data not shown). Conventional cell-based assays that rely on second messenger-induced signals are inherently nonspecific. To confirm that the GPCR/arrestin β-gal complementation was specific, we stimulated cells with unrelated agonists known not to interact with the specific GPCR. This did not result in increased β-galactosidase activity for any of the receptors, validating the assay (data not shown). In summary, the in vitro characterization of all four GPCR cell lines exhibited high sensitivity and specificity, rapid inducibility as well as reversibility, providing evidence that the cells lines constitute useful assays for high-throughput cell-based screening and for evaluating GPCR-mediated signaling pathways.

C. Imaging of GPCR Activation In Vivo

The unique advantages of the GPCR/arrestin-β-gal complementation system suggested that it could be used for measurement of GPCR activation in complex systems such as living animals. Optical in vivo imaging is increasingly used as a tool to assess physiological and pathological processes as well as the pharmacological action of candidate drugs in real time. Existing cell-based assays to monitor GPCR activation are not applicable to in vivo imaging for the following reasons: (1) lack of a specific signal, making tight control of the assay conditions necessary that can only be achieved in vitro (e.g. second messenger-based signal); (2) lack of a suitable signal readout for whole body imaging (e.g. fluorescence translocation). The inherent specificity of the GPCR/arrestin-β-gal complementation system, the high signal to noise ratio and the applicability of the technology to a variety of GPCRs suggested that it could lead to site-specific, real time signal for this purpose.

The present application describes the use of the luminescent substrate Lugal for in vivo bioluminescent imaging of β-gal activity in mice. As discussed above, this assay relies on the sequential action of two reporter enzymes, e.g., β-gal and firefly luciferase (Fluc), making it possible to combine the advantages of both. Lugal, a caged form of D-luciferin, is cleaved by β-gal to generate free D-luciferin that subsequently serves as a substrate for the ubiquitously-expressed Fluc in the final, light-emitting enzymatic step. Thus, luminescence generation is dependent on β-gal activity.

Figure 10:
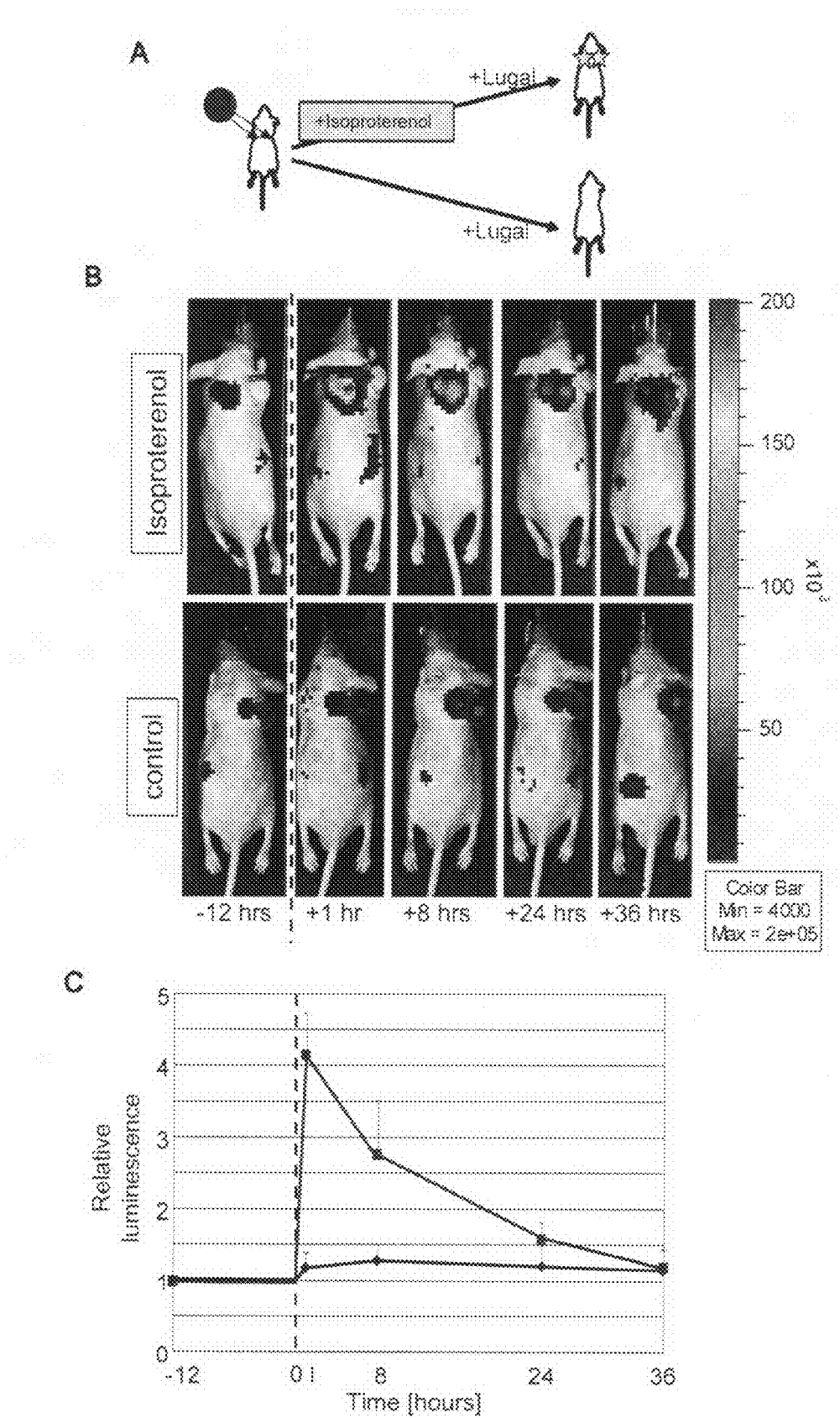
FIG. 10: Luminescent imaging of GPCR activation using GPCR/arrestin-β-gal complementation together with sequential reporter enzyme luminescence. Cells stably transduced with the β2-adrenergic receptor/arrestin-β-gal complementation constructs were transduced to express Fluc and injected in subcutaneous location into the back of BALB/c nude mice (4×10⁶ cells/injection). (A) Seven to fourteen days later, baseline luminescence was imaged by injection of Lugal. Isoproterenol (2 mg/kg i.p.) or vehicle was injected and luminescence imaged again after 1, 8, 24 and 36 hours. (B) Robust increase in luminescence is seen 1 hour after isoproterenol injection that subsequently drops to baseline values within 24 hours. (C) Quantification shows that signal increase was approximately 4-fold over baseline (n=9/group).

To explore the possibility of applying this imaging system to the detection of GPCR activation in living mice, C2C12 cells carrying the β2-adrenoreceptor/arrestin β-galactosidase construct (β2AR cells) were retrovirally transduced to express Fluc as well as the proto-oncogene ras to enhance cell survival. As schematized in FIG. 10A, β2AR/Fluc cells ($4 \times 10^6$) were implanted subcutaneously into the back of Balb/c nude mice. Seven to fourteen days after implantation, baseline bioluminescence images were acquired by intraperitoneal (i.p.) injection of Lugal in a Xenogen IVIS-100 system as previously described. Between 12 and 23 hours later, isoproterenol (6 mg/kg) or vehicle was injected i.p., and imaging was repeated 1, 8, 24 and 36 hours later. A robust, approximately 4-fold increase in luminescence was seen compared with baseline 1 hour after stimulation with isoproterenol (FIG. 10B and FIG. 10C). Luminescence continuously declined thereafter and eventually returned to baseline within 24 to 36 hours. The observed pharmacokinetics are in line with the published serum half life of isoproterenol of approx. 2 hours.

Figure 11:
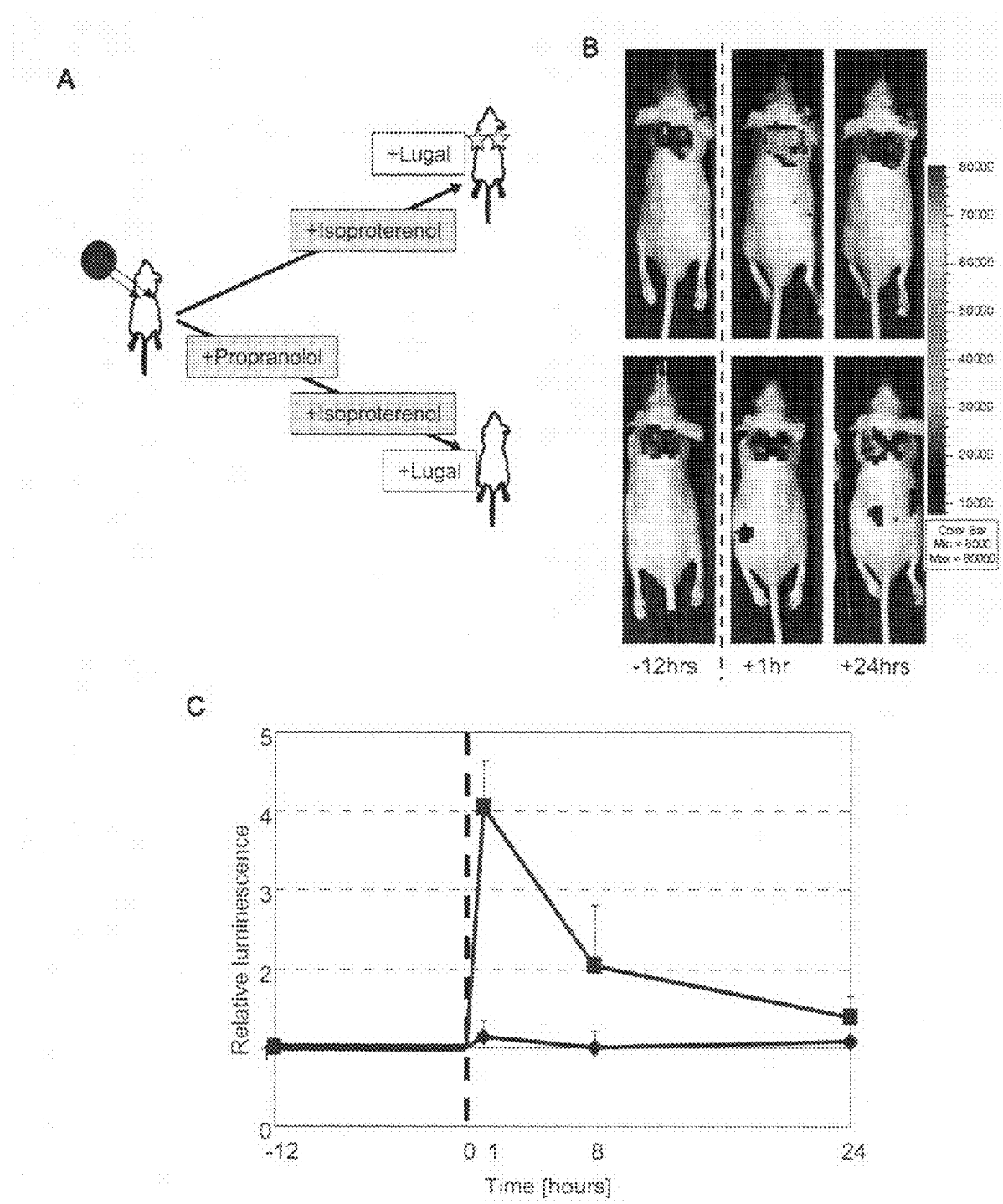
FIG. 11: GPCR activation monitored by GPCR/arrestin-β-gal complementation together with SRL luminescence can be blocked by a specific inhibitor. Cells stably transduced with β2-adrenergic receptor/arrestin-β-gal complementation constructs and were transduced to express Fluc and injected into the back of BALB/c nude mice. (A) Baseline luminescence was acquired by i.p. injection of Lugal. Mice were pre-treated with the β-adrenergic receptor antagonist propranolol or vehicle. One hour later, all mice were injected with the agonist isoproterenol (2 mg/kg i.p.). (B) As before, isoproterenol injection induced a robust luminescence increase. In contrast, propranolol completely inhibited an isoproterenol-induced GPCR activation. (C) As before, isoproterenol induced an approximately 4-fold increase in luminescence, whereas no such effect was seen after pre-treatment with the β-blocker propranolol (n=6/group).

We sought to explore whether this system could be used to assess the effects of inhibitors of β2-adrenoreceptors as well. As schematized in FIG. 11A, Balb/c nude mice were injected with β2AR/Fluc cells as described above. Following acquisition of baseline bioluminescence 7 to 14 days after cell injection, mice were either injected either with propranolol (3 mg/kg i.p.) to inhibit β2-adrenoreceptor activation or vehicle. One hour later, all mice were injected with isoproterenol (6 mg/kg) and imaged 1, 8 and 24 hours later by i.p. injection of Lugal. As shown in FIG. 11B and FIG. 11C, mice pretreated with vehicle alone before injection of isoproterenol showed an approximate 4-fold increase in luminescence, but luminescence generation was completely abrogated in mice that had been pre-treated with propranolol. These experiments show that the isoproterenol-induced β2-adrenoreceptor activation can be effectively inhibited by a β blocker and confirm that the isoproterenol-induced luminescence was specific to β2-adrenoreceptor activation.

Figure 12:
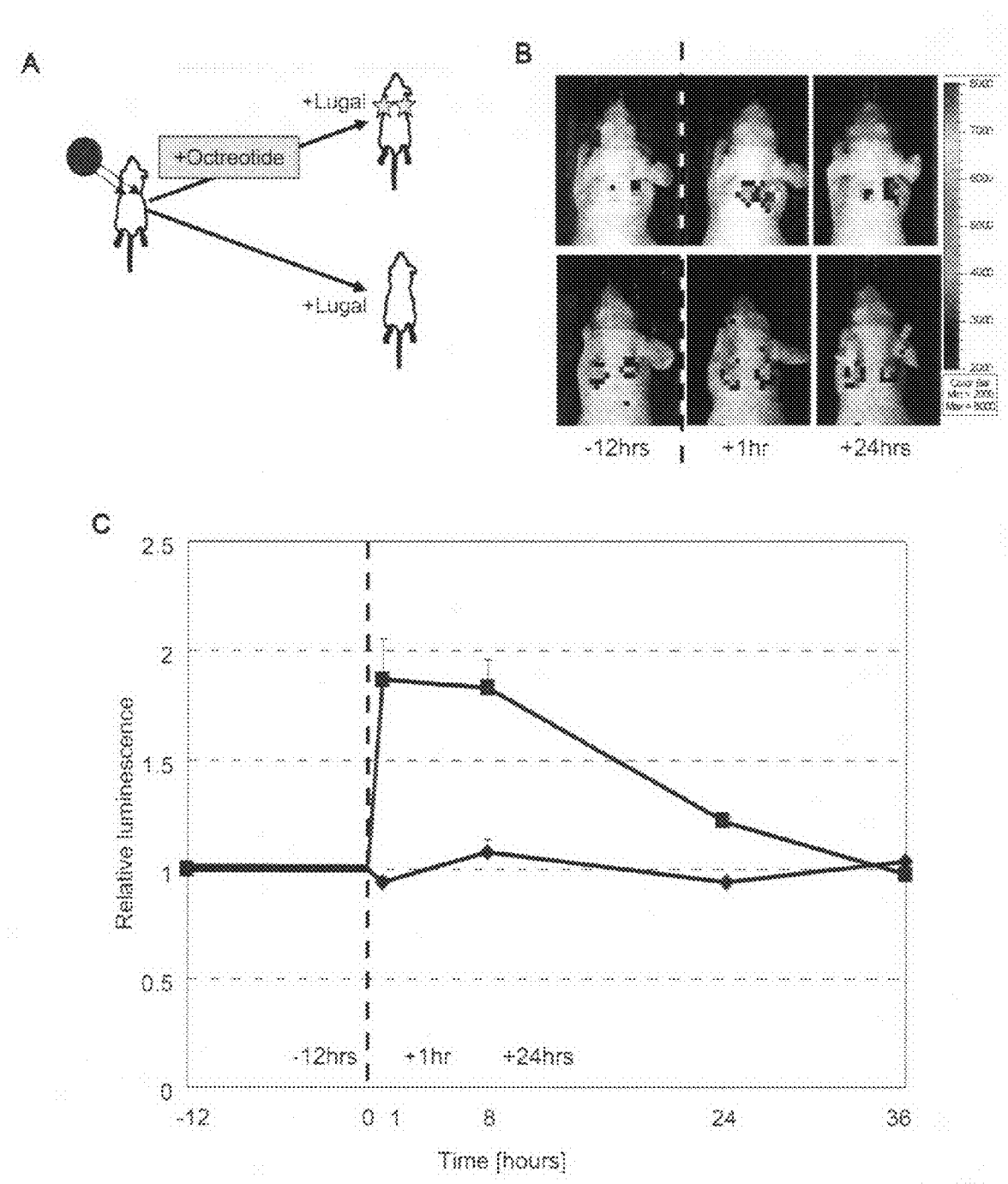
FIG. 12: Luminescent imaging of somatostatin receptor activation in living mice. Cells stably transduced with the somatostatin 2 receptor/arrestin-β-gal complementation constructs were transduced to express Fluc and injected in subcutaneously s into the back of BALB/c nude mice (4×10⁶ cells/injection). (A) Seven to fourteen days later, baseline luminescence was imaged by injection of Lugal. Octreotide (2 mg/kg i.p.) or vehicle was injected and luminescence imaged again after 1, 8, 24 and 36 hours (36 hour time point not shown in A). (B) A robust increase in luminescence is seen 1 hour after isoproterenol injection that subsequently fades to baseline values within 24 hours. (C) Quantification shows that signal increase was approximately 1.8-fold over baseline (n=5/group). Unlike the β2 adrenergic receptor stimulated by isoproterenol, the signal did not decline for more than 8 hours after injection of octreotide, which may be explained by the longer serum half life of octreotide compared with isoproterenol.

Finally, we sought to confirm that agonist-induced luminescence in vivo was not restricted to the β2AR cells, but could be applied to other receptors. We engineered new cell lines carrying the SSTR2/arrestin-β-galactosidase construct by retroviral transduction with the Fluc and ras genes (SSTR2/Fluc). As schematized in FIG. 12A, cell injection and bioluminescent imaging using Lugal were performed as described above. Following acquisition of baseline images, SSTR2 was activated by injection of the small molecule somatostatin analogue Octreotide (0.3 μg/kg i.p.). As shown in FIG. 12B and FIG. 12C, an increase in luminescence by approximately 1.9-fold was seen 1 hour after Octreotide injection. Interestingly, luminescence did not decrease immediately thereafter, but remained elevated at the same level until 8 hours after octreotide injection before finally returning to baseline after 24 hours. Hence, maximum activation of the somatostatin-2 receptor was prolonged compared with that of the isoporterenol-induced activation of β2-adrenergic receptor. This behavior is in line with the long serum half-life of octreotide (approx. 6 hours), a drug specifically developed to provide longer plasma concentrations than the physiological agonist somatostatin.

In summary, the approach of assessing GPCR activation using the low-affinity β-gal complementation tethered to specific GPCRs and α-arrestin in combination with bioluminescent sequential reporter enzyme imaging using the β-galactosidase substrate Lugal made it possible to image activation and inhibition of GPCR in living mice.

III. Discussion

A major stumbling block in drug discovery is the unpredictable in vivo pharmacology of lead compounds and their numerous chemical modifications generated within the process of lead optimization. Key factors that ultimately determine the suitability of a compound as a candidate drug (e.g. target efficacy, distribution, protein binding, clearance and metabolism) can only be roughly estimated by series of in vitro assays in a lengthy, error-prone process that leads to undue pipeline attrition. Clearly, the possibility to measure the pharmacological effect of a larger number of candidate molecules at their target directly and in real-time in living subjects would greatly reduce the strain on resources and increase the accuracy of candidate selection. To this end, radiolabeling of drugs is used to assess their biodistribution, however it requires special and costly facilities, the resolution is low and the procedure provides no information about the pharmacological activity of the compound. Indeed, GPCR activation in a living subject at a given time is the result of the complex interplay of systemic and local agonists and antagonists that cannot be modeled using in vitro methods but needs to be assessed in vivo. For example, β2 adrenergic receptors are directly activated by the endogenous ligands adrenaline (epinephrine) and noradrenaline (norepinephrine). While serum levels of adrenaline and noradrenaline can be easily measured, their local concentration at the receptor or their biologic action on target cells carrying the β2 adrenergic receptors are impossible to determine in vivo. This picture is greatly complicated when pharmacological agents are being evaluated for a number of reasons: (1) β-adrenoreceptor blockers possess intrinsic activity that leads to simultaneous activation and inhibition of the target receptor, at various degrees; (2) β-adrenoreceptor blockers lead to hypotension that triggers the reactive, direct and indirect, upregulation of endogenous β-adrenoreceptor activators, and (3) the highly dynamic nature of events makes determination of circulating levels of therapeutic and endogenous ligands futile. It is surprising that, given the wide clinical application of drugs that directly or indirectly interact with the adrenergic system, assumptions on adrenoreceptor activation need to be entirely derived from in vitro data and from secondary biomarkers (e.g., blood pressure) due to the lack of better monitoring technologies. Clearly, a method that would make it possible to determine the activation of a GPCR of interest in living animals would expedite the in vivo testing of drug candidates.

By coupling the α and ω peptide fragments of the low-affinity β-gal complementation system with different GPCRs and arrestin we have developed a novel assay that can be used for high-sensitivity screening and in vivo luminescent imaging of GPCR activation. Agonist stimulation of the receptor leads to binding of arrestin which forces the complementation of the β-gal fragments leading to enzymatic activity. β-gal provides the advantage of enzymatic amplification that can be read out using a wide variety of substrates, making this technology suitable for many different applications. The binding of arrestin to GPCRs occurs independently of the specific g-protein coupling of the GPCR and thus provides the opportunity for a single technology to be used to detect activation of the majority of GPCRs. In this work we show that the activation of Gs (B2AR and AVPR2) as well as Gi (SSTR2 and AGTR1) coupled receptors can be assayed using the β-gal complementation technology. All four receptors tested attained greater than an 8-fold signal to noise ratio using a homogeneous chemiluminescent assay that is directly applicable to a high-throughput screening environment.

The high signal to noise ratio obtained using our enzyme complementation system in conjunction with a recently developed method of visualizing β-gal activity using bioluminescent imaging suggested that the system could be used to detect GPCR activation in vivo. To accomplish this goal cells were engineered to contain the enzyme complementation arrestin assay together with Fluc and implanted into living mice. We show that activation of the specific GPCR by a systemically administered agonist can be measured non-invasively in these animals within hours using bioluminescent imaging. Importantly the signal can be blocked by pretreatment with an antagonist demonstrating the specificity of the system and suggesting that this technology can be used to testing either inhibitors and stimulators of given GPCRs.

The technology shown here was used as a cell-based system. Thus, it was possible to validate it using agonists and antagonists both in vitro and in vivo using the same cells. Transgenic mice carrying the GPCR and arrestin constructs as described herein may also be employed in the bioimaging applications described above. Alternatively, direct gene transfer, e.g. using plasmids or adeno-associated virus, could be used to integrate the constructs into endogenous-tissue.

In summary, by coupling the α and ω peptide fragments of the low-affinity β-galactosidase complementation system with different GPCRs and arrestin we have developed a novel assay that can be used for high-sensitivity and high throughput screening applications, including in vivo luminescent imaging of GPCR activation. Specifically, we have shown that the sensitivity and specificity of the sequential reporter enzyme luminescent system described herein is sufficient to allow the monitoring of GPCR activation in living mice.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of evaluating the activity of a reporter enzyme associated with an intact cell, said method comprising:
    (a) contacting an intact cell associated with a reporter enzyme with a prosubstrate, wherein said intact cell comprises a luminescent enzyme and wherein said prosubstrate includes:
        (i) a reporter enzyme cleavable domain that is cleavable by said reporter enzyme; and
        (ii) a luminescent enzyme substrate for said luminescent enzyme, wherein said reporter enzyme cleavable domain impairs the ability of said luminescent enzyme substrate from acting as a substrate for said luminescent enzyme; and
    (b) detecting a signal generated from conversion of said luminescent enzyme substrate to a luminescent product by said luminescent enzyme to evaluate the activity of said reporter enzyme.

2. The method according to claim 1, wherein said reporter enzyme is located at an intracellular location of said cell.

3. The method according to claim 1, wherein said reporter enzyme is located at an extracellular location of said cell.

4. The method according to claim 1, wherein said contacting is in vitro.

5. The method according to claim 1, wherein said contacting is in vivo.

6. The method according to claim 1, wherein said cell comprises a nucleic acid coding sequence for said reporter enzyme.

7. The method according to claim 6, wherein said reporter enzyme is operably linked to an inducible promoter.

8. The method according to claim 6, wherein said reporter enzyme is operably linked to a constitutive promoter.

9. The method according to claim 1, wherein said reporter enzyme is conjugated to a targeting moiety.

10. The method according to claim 1, wherein said reporter enzyme is conjugated to a cell.

11. The method according to claim 1, wherein said cell is a mammalian cell.

12. The method according to claim 1, wherein said reporter enzyme is beta-galactosidase.

13. The method according to claim 1, wherein said luminescent enzyme is a luciferase.

14. The method according to claim 1, wherein said luminescent enzyme substrate is luciferin.

15. The method according to claim 1, wherein said signal detected in said method is a luminescent signal.

16. The method according to claim 1, wherein said cell is present in a multicellular organism.

17. The method according to claim 1, wherein the activity of multiple reporter enzymes is evaluated using multiple prosubstrates.

18. The method according to claim 1, wherein the method further comprises contacting said cell with free luciferase substrate.

19. A method of evaluating the activity of a reporter enzyme associated with a cell in vitro, said method comprising:
    (a) contacting a cell associated with a reporter enzyme in vitro with prosubstrate, wherein said cell comprises a luciferase and wherein said prosubstrate includes:
        (i) a reporter enzyme cleavable domain that is cleavable by said reporter enzyme; and
        (ii) a luciferase substrate for said luciferase, wherein said reporter enzyme cleavable domain impairs the ability of said luciferase substrate from acting as a substrate for said luciferase; and
    (b) detecting a signal generated from conversion of said luciferase substrate to a luminescent product by said luciferase to evaluate the activity of said reporter enzyme.

20. The method according to claim 19, wherein said cell comprises a nucleic acid coding sequence for said reporter enzyme.

21. The method according to claim 20, wherein said reporter enzyme is operably linked to an inducible promoter.

22. The method according to claim 20, wherein said reporter enzyme is operably linked to a constitutive promoter.

23. The method according to claim 19, wherein said reporter enzyme is conjugated to a targeting moiety.

24. The method according to claim 19, wherein said cell is a mammalian cell.

25. The method according to claim 19, wherein said reporter enzyme is beta-galactosidase.

26. The method according to claim 19, wherein said luciferase is a firefly luciferase.

27. The method according to claim 19, wherein said luciferase substrate is luciferin.

28. The method according to claim 19, wherein said signal detected in said method is a luminescent signal.

29. The method according to claim 19, wherein the activity of multiple reporter enzymes is evaluated using multiple prosubstrates.

30. A method of evaluating the activity of a reporter enzyme in a multicellular organism, said method comprising:
    (a) administering to a multicellular organism associated with a reporter enzyme a prosubstrate, wherein said multicellular organism comprises a luciferase and wherein said prosubstrate includes:
        (i) a reporter enzyme cleavable domain that is cleavable by said reporter enzyme; and
        (ii) a luciferase substrate for said luciferase, wherein said reporter enzyme cleavable domain impairs the ability of said luciferase substrate from acting as a substrate for said luciferase; and (b) detecting a signal generated from conversion of said luciferase substrate to a luminescent product by said luciferase to evaluate the activity of said reporter enzyme.

31. The method according to claim 30, wherein said reporter enzyme is at an intracellular location.

32. The method according to claim 30, wherein said reporter enzyme is at an extracellular location.

33. The method according to claim 30, wherein said multicellular organism is transgenic for said reporter enzyme.

34. The method according to claim 30, wherein said reporter enzyme has been introduced into said multicellular organism.

35. The method according to claim 34, wherein said reporter enzyme is conjugated to a targeting moiety.

36. The method according to claim 34, wherein said reporter enzyme is associated with a cell.

37. The method according to claim 30, wherein said multicellular organism is a vertebrate.

38. The method according to claim 37, wherein said vertebrate is a mammal.

39. The method according to claim 38, wherein said mammal is a rodent.

40. The method according to claim 30, wherein said reporter enzyme is beta-galactosidase.

41. The method according to claim 30, wherein said luciferase is a firefly luciferase.

42. The method according to claim 30, wherein said luciferase substrate is luciferin.

43. The method according to claim 30, wherein said signal detected in said method is a luminescent signal.

44. The method according to claim 43, wherein said luminescent signal is non-invasively detected.

45. The method according to claim 30, wherein the activity of multiple reporter enzymes is evaluated using multiple pro-substrates.

46. The method according to claim 1, wherein said reporter enzyme is an enzyme complementation reporter system.

47. The method according to claim 46, wherein said enzyme complementation reporter system is a reduced affinity complementation system comprising a first and a second reduced affinity reporter subunit.

48. The method according to claim 47, wherein said method is a method for determining whether a first and second protein interact, wherein said reduced affinity complementation system comprises:
   (1) a first fusion protein of said first protein and said first reduced affinity reporter subunit; and
   (2) a second fusion protein of said second protein and said second reduced affinity reporter subunit;
   wherein said first and second reduced affinity reporter subunits produce a first detectable signal in the absence of an interaction between said first and second protein that is less than a second detectable signal that is observed in the presence of an interaction between said first and second protein.

49. The method according to claim 48, wherein said reduced affinity complementation reporter system comprises complementing subunits of β-galactosidase.

50. The method according to claim 48, wherein said first protein is a G-protein coupled receptor (GPCR) and said second protein is β-arrestin2.

51. The method according to claim 50, wherein said GPCR is selected from the group consisting of: angiotensin receptor 1, somatostatin receptor 2, vasopressin 2 receptor, and β-adrenergic receptor.

* * * * *